US007255998B1

(12) United States Patent
Tashiro et al.

(10) Patent No.: US 7,255,998 B1
(45) Date of Patent: Aug. 14, 2007

(54) HIGH SENSITIVITY IMMUNOASSAY METHOD

(75) Inventors: Kei Tashiro, Kyoto (JP); Tasuku Honjo, Kyoto (JP); Masaya Ikegawa, Kyoto (JP); Kazuko Matsumoto, Setagaya (JP)

(73) Assignee: Japan Science and Technology Corporation, Saitama (JP)

( * ) Notice: Subject to any disclaimer, the term of this patent is extended or adjusted under 35 U.S.C. 154(b) by 637 days.

(21) Appl. No.: 10/089,776

(22) PCT Filed: Sep. 28, 2000

(86) PCT No.: PCT/JP00/06743

§ 371 (c)(1),
(2), (4) Date: Jun. 21, 2002

(87) PCT Pub. No.: WO01/23891

PCT Pub. Date: Apr. 5, 2001

(30) Foreign Application Priority Data

Sep. 29, 1999 (JP) ................................. 11-277629

(51) Int. Cl.
*G01N 33/53* (2006.01)
*G01N 33/532* (2006.01)
*G01N 33/533* (2006.01)
*G01N 33/24* (2006.01)
*G01N 21/76* (2006.01)
*G01N 33/547* (2006.01)
*C07K 1/10* (2006.01)

(52) U.S. Cl. ..................... 435/7.1; 435/7.5; 435/968; 435/975; 435/7.92; 435/970; 436/544; 436/546; 436/87; 436/172; 436/532; 530/402

(58) Field of Classification Search ................ 435/7.1, 435/975, 7.5, 968, 7.92, 970; 436/544, 546, 436/172, 532, 87; 568/331; 530/402
See application file for complete search history.

(56) References Cited

U.S. PATENT DOCUMENTS 4,680,275 A * 7/1987 Wagner et al. ............ 436/518
5,859,297 A    1/1999 Matsumoto et al.

FOREIGN PATENT DOCUMENTS

| CA | 1330061     | 6/1994 |
| CA | 2 187 690   | 5/2003 |
| EP | 0 794 174 A2 | 9/1997 |
| JP | 60-24450    | 2/1985 |
| JP | 03-251763   | 11/1991 |
| JP | 04-066871   | 3/1992 |
| JP | 9-241233    | 9/1997 |

OTHER PUBLICATIONS

"Macrophage-like RAW 264 cell line and time-resolved fluoroimmunoassay (TRFIA) as tools in screening drug effects on cytokine secretion", Pennanen, et al., Int. J. Immunopharmacol. Jun. 1995; 17(6); 475-80 (1 page).
"Preparation of europium-streptavidin in a time-resolved fluoroimmunoassay for interleuken-3", Knopf, et al., Journal of Immunological Methods, 138 (1991) 233-236 (4 pages).
"A novel and sensitive method for the detection of secreted cell products using time-resolved fluorescence", Ruedl, et al., Journal of Immunological Methods, 168 (1994) 61-67 (7 pages).
"A New Tetradentate B-Diketonate-Europium Chelate That Can Be Covalently Bound to Proteins for Time-Resolved Fluoroimmunoassay", Yuan, et al., Annal. Chem. 1998, 70, 596-601 (6 pages).
"Highly Sensitive Time-Resolved Fluoroimmunoassay of Human Immunoglobulin E by Using a New Europium Fluorescent Chelate as a Label", Yuan, et al., Analytical Biochemistry 254, 283-287 (1987), Article No. AB972444 (5 pages).
Copy of corresponding Korean Office Action dated Apr. 11, 2005 (3 pages).
Copy of corresponding European Office Action dated Mar. 15, 2005 (4 pages).
"Establishment of Time-Resolved Immunofluorometric Assay of Interferon-gamma", by Erdeni, et al., Development in Biochemistry and Biophysics, 1999.26(4), pp. 388-391.
Copy of Chinese Office Action dated Nov. 7, 2003.
Edward J. Leonard, "Plasma Chemokine and Chemokine—Autoantibody Complexes in Health and Disease," Copyright 1996 by Academic Press, Inc.

* cited by examiner

*Primary Examiner*—Long V. Le
*Assistant Examiner*—Shafiqul Haq
(74) *Attorney, Agent, or Firm*—Snell & Wilmer L.L.P.

(57) ABSTRACT

A method for detecting a cytokine in a biological fluid sample with a high sensitivity is provided. A time-resolved fluoroimmunoassay (TR-FIA) method including a step of forming on a solid phase a composite in which a cytokine is captured and which includes a fluorescent structural portion which has been complexed with a lanthanoid metal ion, and measuring fluorescence of the fluorescent structural portion. The composite is formed of a structure in which (a) a first antibody including a portion bound to a solid phase and a region bindable to a cytokine; (b) the cytokine; (c) a second antibody including a region bindable to the cytokine and a portion to which biotin is bound; (d) a conjugate including streptoavidin or avidin and a fluorescent structural portion capable of being complexed with a lanthanoid metal ion; and (e) the lanthanoid metal ion are bound. The fluorescent structural portion is represented by General Formula (I):
$R-Ar-C(=O)-CH_2-C(=O)-C_nF_{2n}-X$.

14 Claims, 15 Drawing Sheets

HIGH SENSITIVITY IMMUNOASSAY METHOD

RELATED APPLICATIONS

This is a US national phase filing under 35 U.S.C. §371 of PCT/JP00/06743 filed Sep. 28, 2000 and claims priority from JP 11-277629 filed Sep. 29, 1999.

TECHNICAL FIELD

The present invention relates to a time-resolved fluoroimmunoassay (TR-FIA) method for detecting cytokines in a biological fluid sample, and in particular to an assay method for highly sensitively detecting cytokines in a biological fluid sample by utilizing a fluorescent europium complex.

BACKGROUND ART

The concentration of free cytokines or chemokines present in a normal biological fluid such as human plasma is near or below the detection limit of conventional ELISA assays. For example, it has been reported that a conventional ELISA assay whose detection limit is about 6 picomols (pM) cannot detect IL-8 from within normal human plasma (Leonard et al. (Document 1)). Enhancement of measurement sensitivity and reduction of the non-specific background associated with the biological fluid sample are chief problems to be solved in order to attain accurate measurement of chemokine concentration in a biological fluid sample.

In recent years, a time-resolved fluoroimmunoassay method which utilizes a europium complex has been developed, and is being used in clinical applications (Kropf et al., (Document 2)). The radiation wavelength (615 nm) of a free, complexed europium ion ($Eu^{3+}$) is not influenced by the excitation wavelength (340 nm) or by a transient background fluorescence (350 to 600 nm) associated with a certain type of protein, which is convenient. One type of analysis method which is based on this principle is commercialized as DELFIA (dissociation-enhanced lanthanoid fluoroimmunoassay; Pharmacia), and is utilized in assays of TNF α and IL-6. However, DELFIA has not been successful in accurately measuring the concentration of such cytokines in plasma (Ogata et al. (Document 3)).

Recently, a group led by Matsumoto has developed a 4,4'-bis(1'',1'',2'',2'',3'',3'',-heptafluoro-4'',6'',-hexanedion-6''-yl)-sulpho-o-terphenyl(BHHCT)-$Eu^{3+}$ complex as a labeling compound. This complex is capable of directly binding to proteins, and allows for highly sensitive analysis via a time-resolved type fluorescence measurement (Yuan et al. ('97)(Document 4) and Yuan et al. ('98)(Document 5)). BHHCT has a β-diketone structure, and has a binding stability constant with respect to $Eu^{3+}$ as high as $10^{10}M^{-1}$. A resultant $Eu^{3+}$ complex exhibits quite excellent properties, as evidenced by a lifetime which exceeds 400 microseconds (μs), and absorption and emission wavelength maximals of 330 nm and 615 nm. This complex has been indicated to be useful for the detection of α-fetoprotein (Yuan et al. ('98) (Document 5) and immunoglobulin E (IgE) Yuan et al.('97) (Document 4)), which are tumor markers in human plasma. However, no instances are known in which such an $Eu^{3+}$ complex has been applied to the detection of cytokines in a biological fluid sample.

Stromal cell-derived factor-1 (SDF-1) is a cytokine belonging to the chemokine family, which was first cloned from a stromal cell line in 1993 (Tashiro et al. (Document 6)). SDF-1 is a chief ligand for a CXCR4 receptor (Bleul et al. (Document 7) and Oberlin et al. (Document 8)). This receptor is known to function as a CD4 co-receptor for a subgroup of human immunodeficiency virus type 1 (HIV-1). Furthermore, recent study has shown that polymorphism of the SDF-1 gene is involved in slowing of the progression of acquired immunodeficiency syndrome (AIDS) (e.g., Winkler et al. (Document 9) and Martin et al. (Document 10)). However, its functional mechanism admits of several theories, and is yet to be established.

It has also been pointed out that SDF-1 plays an essential role in embryogenesis of the hematopoietic, cardiovascular, and nervous systems (e.g., Zou et al. (Document 11) and Tachibana et al. (Document 12)). On the other hand, many of the biological functions of SDF-1 in adult tissue are still unknown.

As described above, it is extremely important for advancement of the understanding of SDF-1 to develop a technique for accurately quantifying and monitoring SDF-1 in a biological fluid sample. It is needless to say that an accurate measurement method in biological fluid samples would similarly make academic and clinical contributions in other chemokines and cytokines as well. From this perspective, an assay method for detecting cytokines with a higher sensitivity is desired.

DISCLOSURE OF THE INVENTION

The present invention aims to solve the aforementioned problems, and provides a method for detecting cytokines in a biological fluid sample with a higher sensitivity and ease.

According to the present invention, there is provided a time-resolved fluoroimmunoassay (TR-FIA) method for detecting a cytokine in a biological fluid sample, comprising:

forming a composite in which (a) a first antibody including a portion bound to a solid phase and a region bindable to a cytokine: (b) the cytokine; (c) a second antibody including a region bindable to the cytokine and a portion to which biotin is bound; (d) a conjugate including streptoavidin or avidin and a fluorescent structural portion capable of being completed with a lanthanoid metal ion; and (e) the lanthanoid metal ion are bound, the composite being formed on the solid phase; and measuring fluorescence of the fluorescent structural portion which has been complexed with the lanthanoid metal ion, wherein the fluorescent structural portion is represented by General Formula (I):

$$—R—Ar—C(=O)—CH_2—C(=O)—C_nF_{2n}—X \qquad (I)$$

(where R is a residue which is a functional group capable of forming a covalent bond with a protein; Ar is a hydrocarbon group having a conjugated double bond system; n is an integer equal to or greater than 1; and X is a fluorine atom or a group represented by General Formula (II):

$$—C(=O)—CH_2—C(—O)—Ar—R \qquad (II).$$

In one embodiment of the present invention, the lanthanoid metal ion may be europium.

In one embodiment of the present invention, the fluorescent structural portion may be represented by General Formula (III):

$$—R—Ar—(C(=O)—CH_2—C(=O)—C_nF_{2n+1})_2 \qquad (III)$$

(where R, Ar, and n have the same definitions as above).

In one embodiment of the present invention, the fluorescent structural portion may be 4,4'-bis(1",1",1",2",2",3",3"-heptafluoro-4",6"-hexanedion-6"-yl)-sulpho-o-terphenyl.

In one embodiment of the present invention, 10 to 60 units of the fluorescent structural portion may be present per molecule of streptoavidin or avidin in the conjugate.

In one embodiment of the present invention, the step of measuring fluorescence may be performed without allowing the composite formed on the solid phase to dissociate.

In another embodiment of the present invention, the step of measuring fluorescence may be performed after allowing the composite formed on the solid phase to dissociate.

In one embodiment of the present invention, the cytokine may be a cytokine belonging to the chemokine family.

In one embodiment of the present invention, the cytokine may be a CXC chemokine.

In one embodiment of the present invention, the cytokine may be stromal cell-derived factor-1 (SDF-1).

Alternatively, in one embodiment of the present invention, the cytokine may be a cytokine which exist as a soluble factor in blood circulation and has a biological activity in a minuscule amount.

Alternatively, in one embodiment of the present invention, the cytokine may be a granulocyte-macrophage-colony stimulating factor (GM-CSF) or interleukin 2 (IL-2).

In one embodiment of the present invention, the biological fluid sample may be plasma or whole blood.

In one embodiment of the present invention, a step of diluting the biological fluid sample with a buffer solution used for sample dilution may be further comprised before the step of forming the composite, and the buffer solution used for sample dilution may be 0.01 to 0.1 M tris-hydrochloric acid whose pH is 7.3 to about 8.3, the buffer solution containing 0.1 to 0.3% of bovine serum albumin, 0.05 to 0.2% of sodium azide, and 0.5 to 1.5% of sodium chloride.

In one embodiment of the present invention, a step of subjecting the biological fluid sample to a heat treatment under non-denaturing temperature conditions for the cytokine may be further comprised before the step of forming the composite.

In one embodiment of the present invention, a step of washing the composite formed on the solid phase with a buffer solution used for washing may be further comprised before the step of measuring fluorescence, and the buffer solution used for washing the composite may be 0.01 to 0.1 M tris-hydrochloric acid whose pH is 8.5 to about 9.5, the buffer solution containing 0.01 to 0.1% polyoxyethylenesorbitan monolaurate.

In one embodiment of the present invention, the solid phase may be a microtiter plate having an IgG adsorption ability of 50 to 200 ng/cm$^2$.

Moreover, according to the present invention, there is provided a kit for a time-resolved fluoroimmunoassay (TR-FIA) method for detecting a cytokine in a biological fluid sample, comprising: a first antibody including a portion bound to a solid phase and a region bindable to a cytokine; a second antibody including a region bindable to the cytokine and a portion to which biotin is bound; a conjugate including streptoavidin or avidin and a fluorescent structural portion capable of being complexed with a lanthanoid metal ion; and the lanthanoid metal ion, wherein the fluorescent structural portion is represented by General Formula (I):

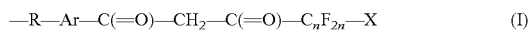

—R—Ar—C(=O)—CH$_2$—C(=O)—C$_n$F$_{2n}$—X     (I)

(where R is a residue which is a functional group capable of forming a covalent bond with a protein; Ar is a hydrocarbon group having a conjugated double bond system; n is an integer equal to or greater than 1; and X is a fluorine atom or a group represented by General Formula (II):

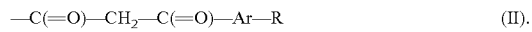

—C(=O)—CH$_2$—C(=O)—Ar—R     (II).

After IL-8 was added to plasma samples, cell pellets or plasma was mixed therewith. After incubation at 37° C. for 15 minutes, the soluble IL-8 within the plasma was quantified. Blank squares represent reference samples which were not mixed with cell pellets or plasma; black circles represent samples which were mixed with plasma; and blank circles represent samples which were mixed with cell pellets. The data indicate average values of quadruplicate measurements.

Figure 4A:
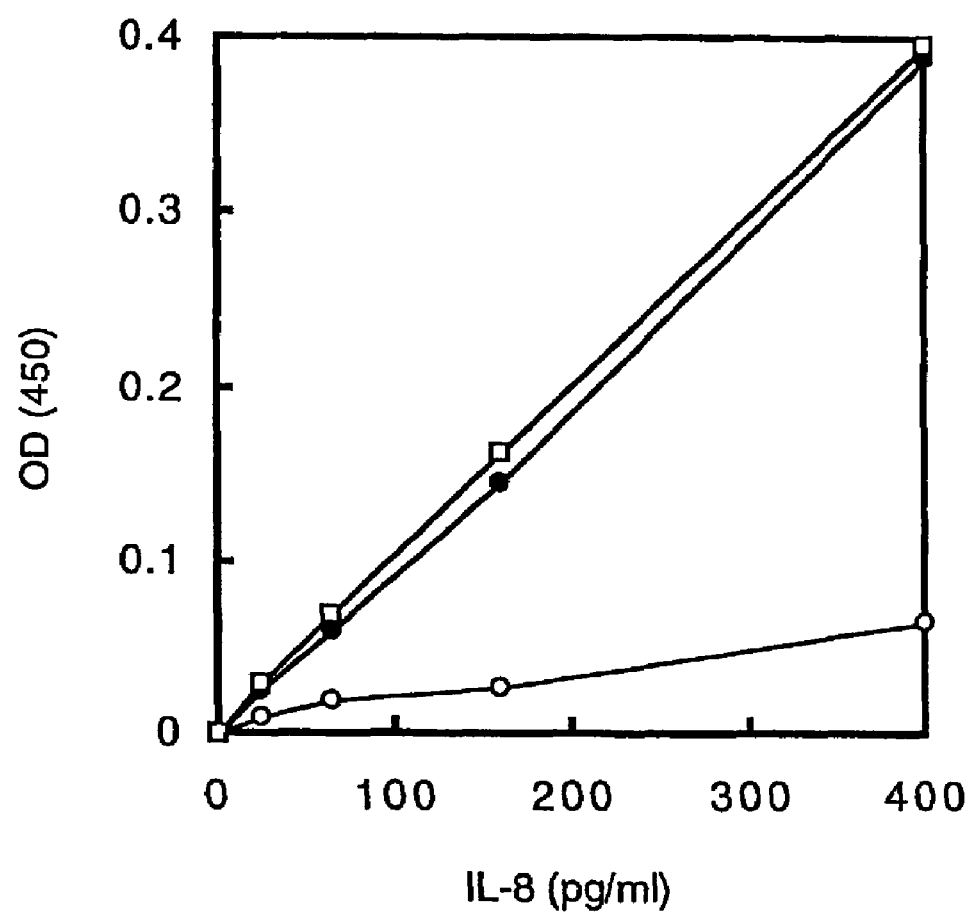
FIG. 4a is a graph illustrating influences of blood cells on an ELISA quantification of IL-8, as a control for SDF-1.
Figure 4B:
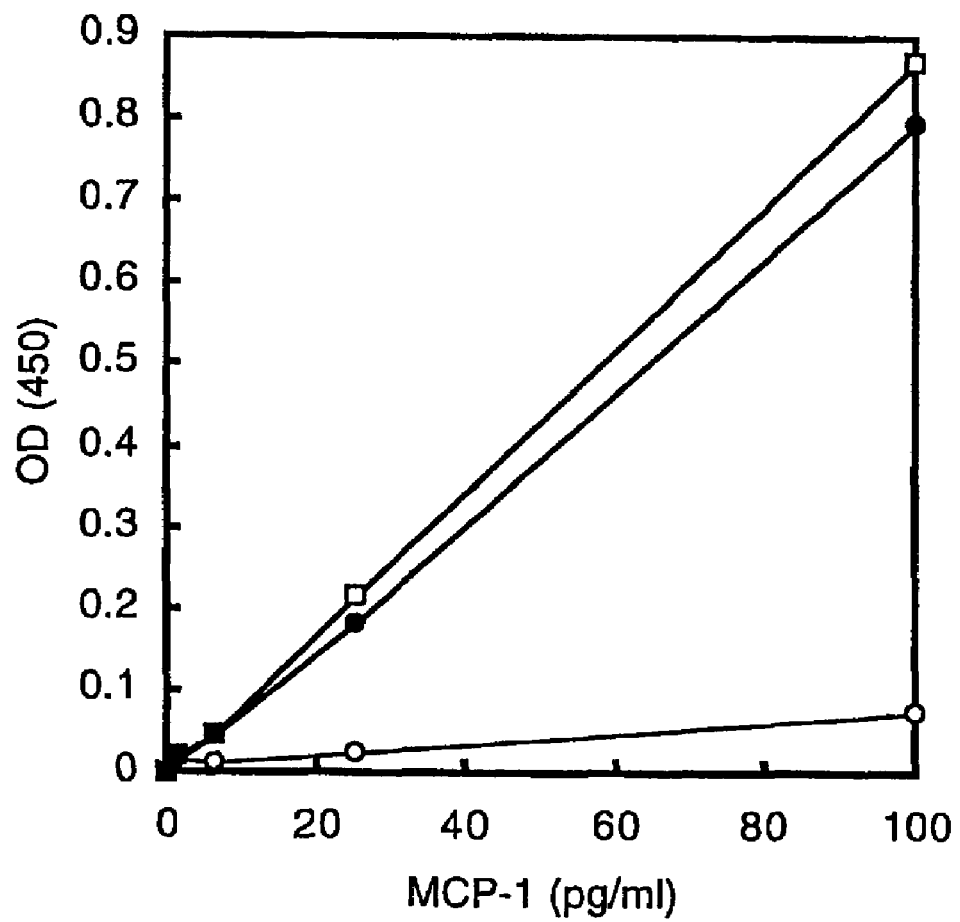

FIG. 4b is a graph illustrating influences of blood cells on an ELISA quantification of MCP-1, as a control for SDF-1. After MCP-1 was added to plasma samples, cell pellets or plasma was mixed therewith. After incubation at 37° C. for 15 minutes, the soluble MCP-1 within the plasma was quantified. The symbols are similar to those in FIG. 4a. The data indicate average values of quadruplicate measurements.

Figure 4C:
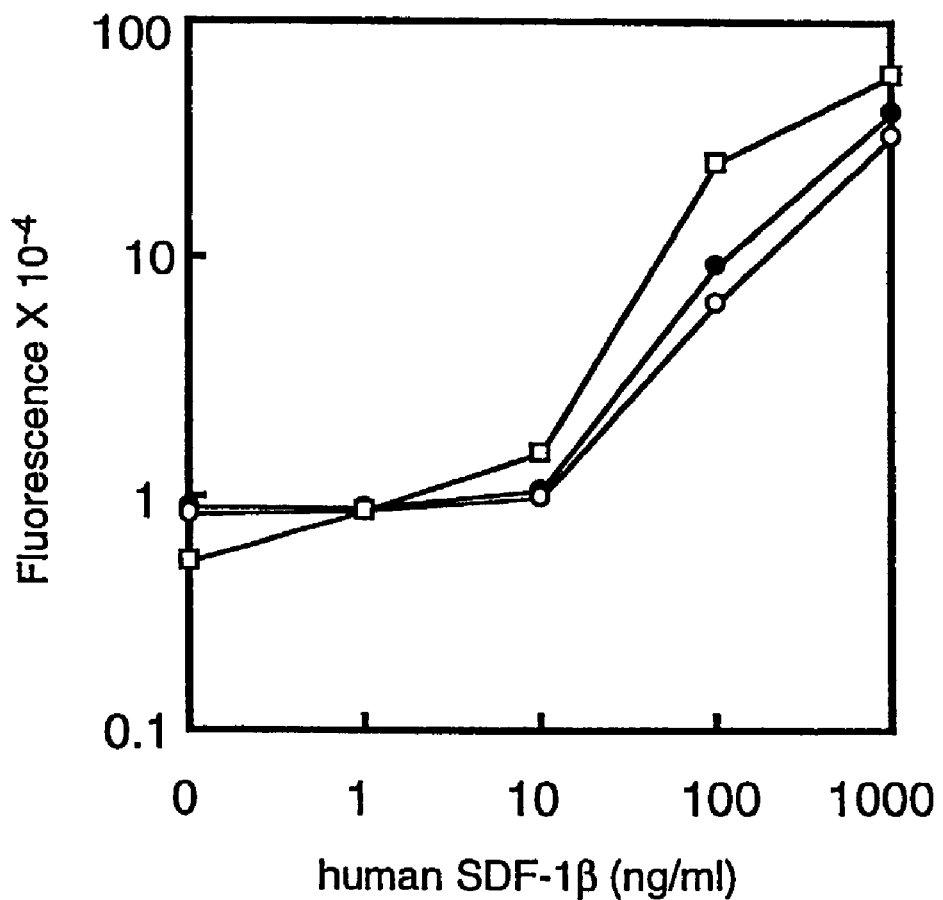

FIG. 4c is a graph illustrating influences of blood cells on a TR-FIA quantification of SDF-1. After SDF-1 was added to plasma samples, cell pellets or plasma was mixed therewith. After incubation at 37° C. for 15 minutes, the soluble SDF-1 within the plasma was quantified. The symbols are similar to those in FIG. 4a. The data indicate average values of quadruplicate measurements.

Figure 5:
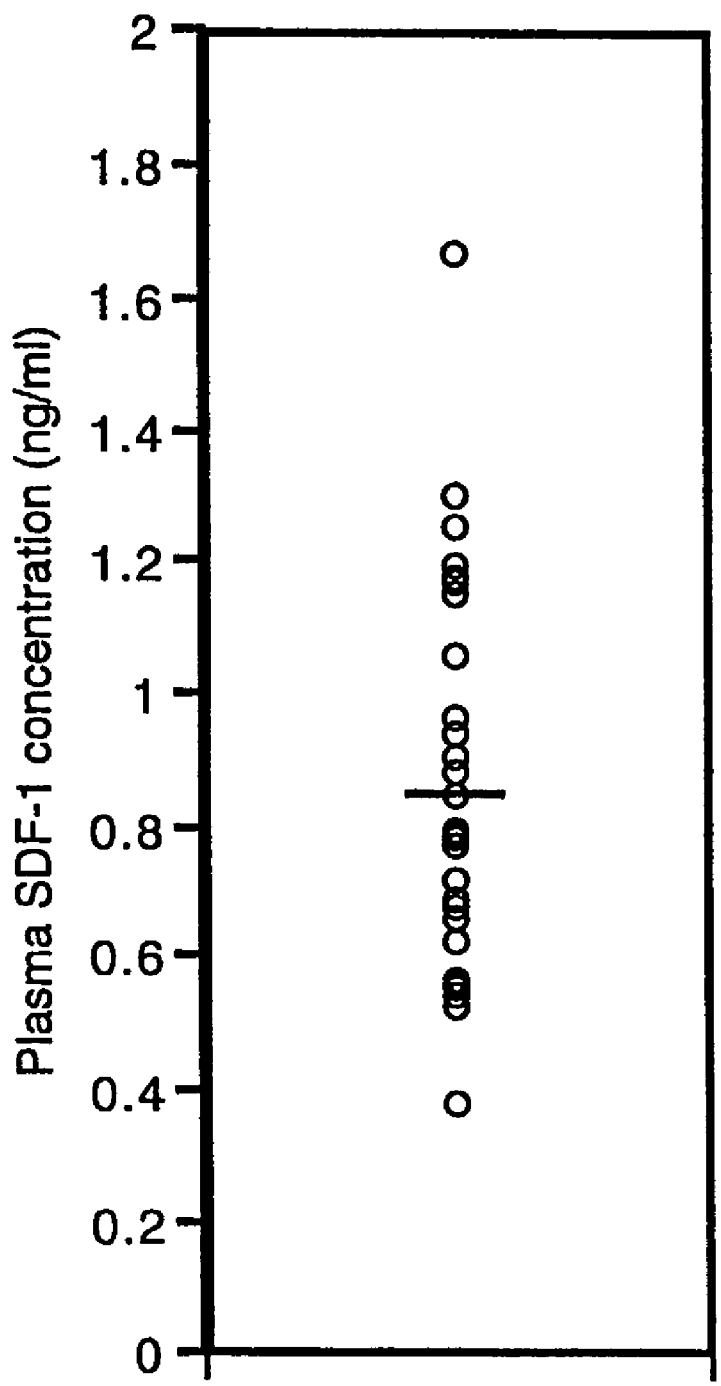

FIG. 5 is a graph illustrating SDF-1 levels in human plasma from 36 healthy Japanese volunteers. All plasma samples were subjected to a heat treatment at 55° C. for 30 minutes before the assay. The data indicate average values of triplicate measurements from two separate measurings.

Figure 6:
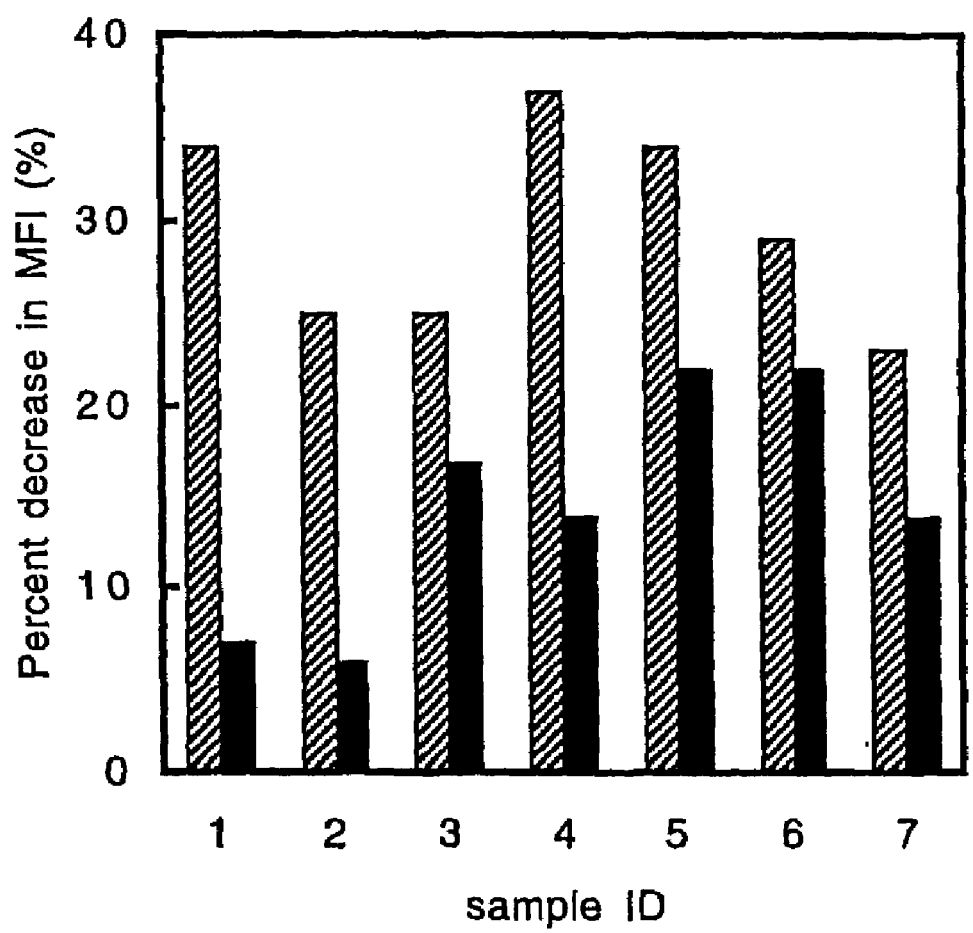

FIG. 6 is a graph illustrating the influences of IgG depletion due to protein G-sepharose on human plasma samples. Plasma samples from 7 healthy Japanese volunteers were incubated on ice with protein G-sepharose for 30 minutes and centrifuged, and the SDF-1 amount in supernatants were measured. Hatched bars and black bars represent unheated samples and heated samples (55° C. for 30 minutes), respectively.

Figure 7:
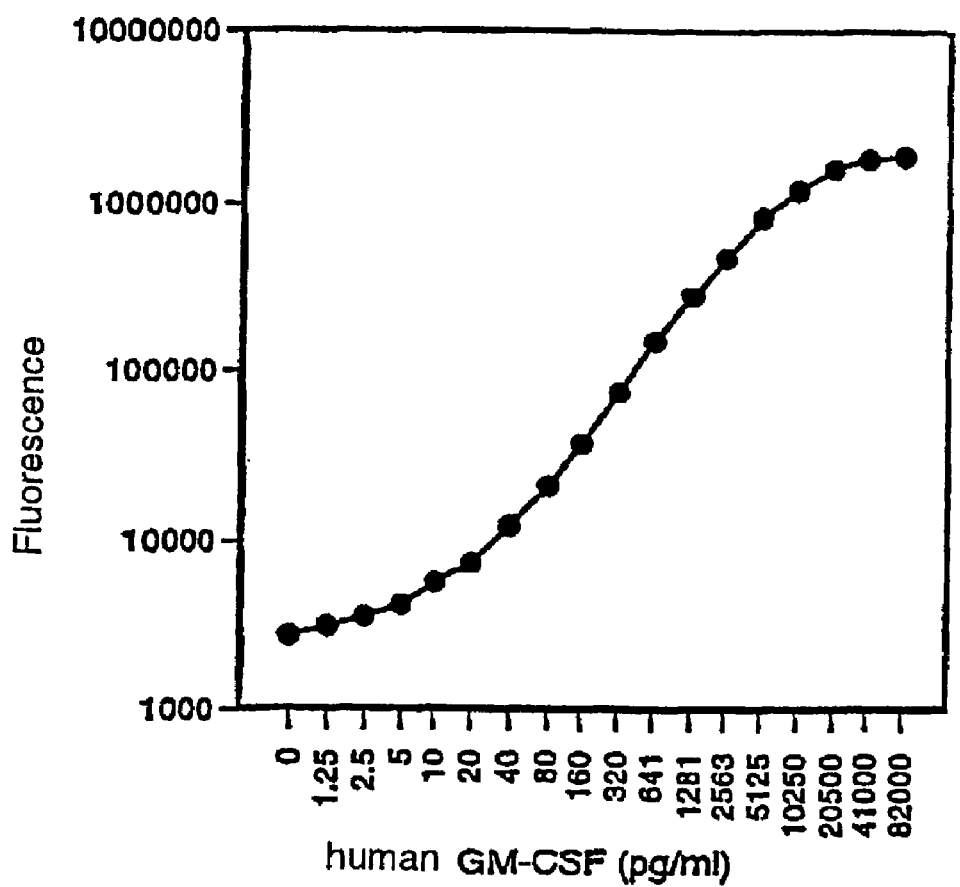

FIG. 7 is a graph illustrating a calibration curve for GM-CSF. A reference GM-CSF was measured by a TR-FIA method. The data indicate average values of triplicate measurements.

Figure 8:
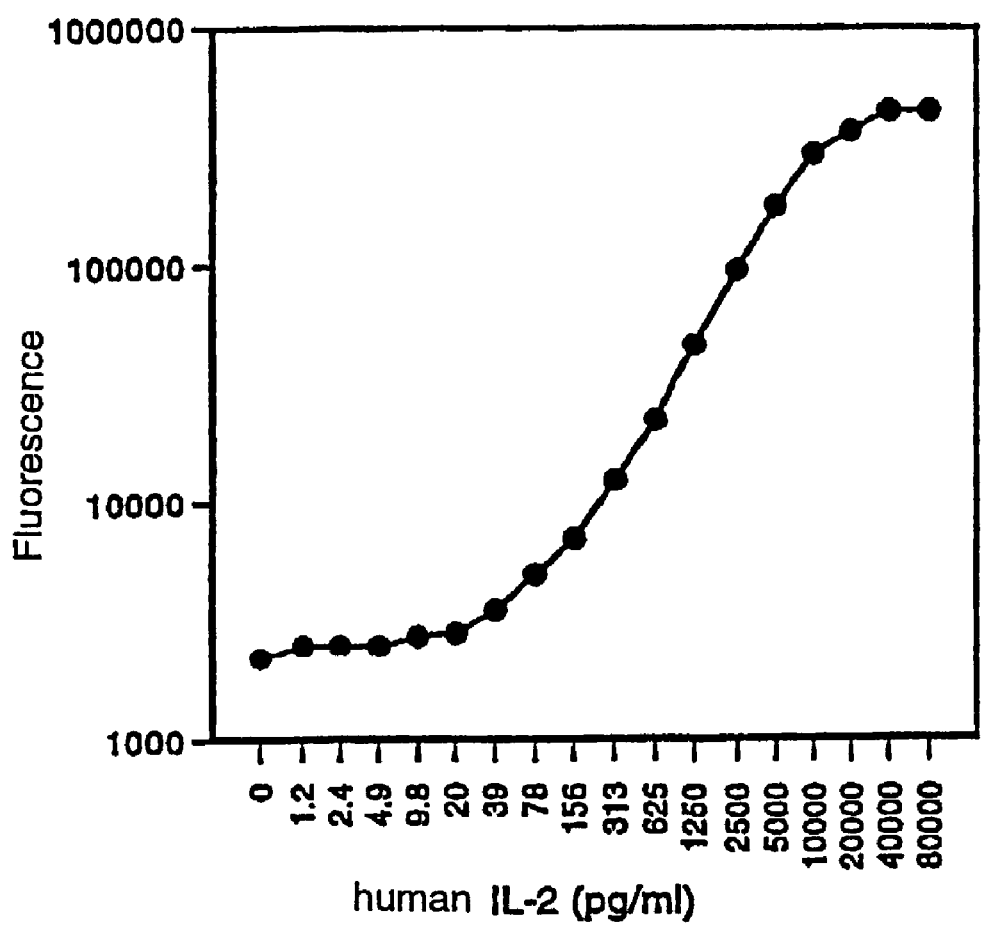

FIG. 8 is a graph illustrating a calibration curve for IL-2. A reference IL-2 was measured by a TR-FIA method. The data indicate average values of triplicate measurements.

BEST MODES FOR CARRYING OUT THE INVENTION

Hereinafter, the present invention will be described in more detail.

The method of the present invention is based on a time-resolved fluoroimmunoassay (TR-FIA) technique. A "time-resolved fluoroimmunoassay" refers to an assay method which labels a measurement subject with a fluorescent compound that is capable of radiating long-life fluorescence, e.g., a lanthanoid metal ion complex according to the present invention, through an immunological reaction, and taking time-resolved type measurements of a fluorescent signal from the labeled subject after the background fluorescence having a shorter life time has disappeared.

The method according to the present invention is particularly suitable for a highly sensitive detection of cytokines in a biological fluid sample. A "biological fluid sample" refers to liquid matter which is collected from a living animal, preferably a mammal, and in particular a human. Representative examples thereof include blood (i.e., whole blood) and its fractions or plasma and serum, as well as cerebral spinal fluid, bile, amniotic fluid, pleural fluid, ascites, tracheobronchial secretion, marrow fluid, milk, lacrimal fluid, nasal discharge, endocardial fluid, intra-articular fluid, saliva, semen, urine, and the like. Furthermore, biological fluid samples may also include supernatants of cultured cells of animal origin and the like. In the method according to the present invention, remarkable effects can be provided when using whole blood, plasma, serum, or cerebral spinal fluid, and in particular when using whole blood or plasma. For convenience, a biological fluid sample, as used herein, includes both a biological fluid itself and a liquid sample which has been subjected to a treatment such as dilution in a carrier which is suitable for the biological fluid.

A "cytokine" refers to a proteinaceous chemical substance which is responsible for information transmission between cells in a living organism. For each individual cytokine, a characteristic receptor is expressed on the surface of a target cell. Binding to such a receptor results in the manifestation of physiological activities such as cell growth and differentiation. A group of cytokines collectively referred to as "hematopoietic factors", which induce the differentiation and growth of blood cells, include colony stimulating factors (CSFs) including granulocyte-macrophage-colony stimulating factors (GM-CSFs), stem cell factors, erythropoietin, thrombopoietin, and the like. Interleukins which control lymphocytes include IL-2, IL-4, IL-5, IL-10, IL-12, IL-13, IL-18, and the like. A group of cytokines collectively referred to as "growth factors" include the TGF-β family, the EGF family, the FGF family, the IGF family, the NGF family, blood platelet-derived growth factors (PDGFs), hepatic cell growth factors (HGFs), vascular endothelial cell growth factors (VEGFs), and the like. A group of cytokines collectively referred to as "tumor necrosis factors" include TNF-α, TNF-β, and the like. A group of cytokines collectively referred to as "interferons" include INF-α, INF-β, INF-γ, and the like. Other known cytokines include endotheline, glial cell-derived neurotrophic factors (GDNFs), and the like. A group of cytokines which impart chemotaxis to any one of functionally mature blood cells are particularly referred to as chemokines. Depending on the conserved cysteine location at their N-terminus regions, chemokines are classified into four categories: CC, CXC, C, or CXXXC.

The detection subject for the method according to the present invention may be any one of the aforementioned cytokines. Furthermore, any newly discovered members of any one of the aforementioned groups of cytokines, or any newly discovered cytokines which do not belong to any one of the aforementioned groups of cytokines, may also be detection subjects for the method according to the present invention. In particular, the method according to the present invention is applicable to cytokines which exist as soluble factors in blood circulation, have a biological activity in minuscule amounts, and are involved in various pathologies.

An example of a detection subject for the method according to the present invention may be cytokines belonging to the aforementioned chemokine family, and in particular CXC chemokines, but is not necessarily limited to such categories. A most preferable example of a detection subject for the method according to the present invention is SDF-1.

In the method according to the present invention, in order to selectively capture and label a desired cytokine in a biological fluid sample, a composite containing that cytokine is formed on a solid phase. Specifically, a cytokine-containing composite is formed from the following components on an appropriate solid phase:

(a) a first antibody including a portion bound to a solid phase and a region bindable to a cytokine;

(b) the cytokine;

(c) a second antibody including a region bindable to the cytokine and a portion to which biotin is bound;

(d) a conjugate including streptoavidin or avidin and a fluorescent structural portion capable of being complexed with a lanthanoid metal ion; and (e) the lanthanoid metal ion.

Hereinafter, the respective components will be described.

As the "solid phase", a solid substance of any shape and material may be used so long as it allows an antibody to bind thereto and does not hinder the formation of the aforementioned conjugate and the fluorescence measurement (described later). For convenience of performing the assay method, a microtiter plate of a multiwell type is typically used, but any other configuration may be used such as a column filled with beads (where the material of the beads may be sepharose, agarose, etc., although not limited thereto). According to the present invention, a microtiter plate which exhibits an intermediate protein adsorption ability may be particularly suitable. As used herein, an "intermediate protein adsorption ability" refers to a property which exhibits typically about 50 to about 200 $ng/cm^2$, preferably about 15 to 150 $ng/cm^2$, and more preferably about 90 to about 120 $ng/cm^2$ when immunoglobulin G (IgG) is adsorbed as a reference protein. The material of the microtiter plate may preferably be polystyrene, although not limited thereto.

Component (a), or the "first antibody", is an antibody which exists in a bound state to the aforementioned solid phase and which is capable of binding to a desired cytokine through an antigen-antibody reaction. In this sense, the first antibody is also referred to as a "capture antibody". In the present specification, an "antibody" is meant to include an immunoglobulin (Ig) and an immunoglobulin-derived molecule of any type, e.g., a polyclonal antibody, a monoclonal antibody, Fab, $(Fab)_2$, or a chimeric antibody. The term "antibody" is used with a broad meaning, and so long as being capable of binding to a cytokine in a manner similar to an immunoglobulin, even includes a receptor having that cytokine as a ligand. An example of a preferable antibody is a polyclonal antibody or a monoclonal antibody. Antibodies to various cytokines are commercially available from, for example, R&D System Inc. (Minnesota, US), Dako Immunoglobulins a/s (Denmark), PharMingen (California, US), Southern Biotechnology Associates (Alabama, US), and the like. Alternatively, an antibody to a desired cytokine can be created by using usual methods such as animal immunization or hybridoma techniques.

Binding to the solid phase can be achieved following usual methods, e.g., by directly coating the first antibody onto a microtiter plate. The "portion bound to a solid phase" of the first antibody typically refers to an Fc region of an antibody which is partially adsorbed to a solid phase, although not limited thereto. For example, a bifunctional linker molecule which is capable of binding to the solid phase and to a portion of the antibody can be used.

Component (b), or a desired cytokine which is present in a biological fluid sample is immobilized to the solid phase, typically by binding to the first antibody. The cytokine does not need to be in a free state to be in contact with the first antibody. For example, the cytokine may bind to the first antibody after binding to the second antibody (described later). Thus, the conjugate formation according to the present invention is not limited with respect to the order of binding of the respective components.

The inventors found that it is essential for highly sensitive cytokine detection that the biological fluid sample containing a desired cytokine is diluted to an appropriate concentration in an appropriate buffer solution before being exposed to an antibody which is capable of binding to that cytokine. The dilution ratio by the biological fluid sample buffer solution may typically be about 1:1 to about 1:30, preferably about 1:2.5 to about 1:20, and more preferably about 1:5 to about 1:15, as represented on a volume basis of (biological fluid sample:buffer solution). The optimum value of the dilution ratio may vary depending on the kind of biological fluid sample and the kind of cytokine, etc., and further on the composition of the buffer solution used for sample dilution.

An appropriate buffer solution used for sample dilution is an alkalescent buffer solution which is composed of tris (hydroxymethyl)aminomethane (abbreviated as "Tris") and an inorganic acid, and typically a tris-hydrochloric acid, whose pH is typically about 7.0 to about 8.6, preferably about 7.3 to about 8.3, and more preferably about 7.5 to about 8.1, and whose concentration is typically about 0.005 to about 0.2 mol(M), preferably about 0.01 to about 0.1 M, and more preferably about 0.025 to about 0.075 M.

The buffer solution used for sample dilution further contains appropriate amounts of a plasma protein component and salts. The plasma protein component is typically serum albumin and preferably bovine serum albumin (BSA), whose concentration is typically about 0.05 to about 0.5%, preferably about 0.1 to about 0.3%, and more preferably about 0.15 to about 0.25%. The salts are typically sodium azide ($NaN_3$) and sodium chloride (NaCl). The concentration of $NaN_3$ may typically be about 0.02 to about 0.4%, preferably about 0.05 to about 0.2%, and more preferably about 0.05 to about 0.15%. The concentration of NaCl may typically be about 0.2 to about 3%, preferably about 0.5 to about 1.5%, and more preferably about 0.6 to about 0.12%.

It will be appreciated that the composition of the buffer solution used for sample dilution is not limited to the aforementioned conditions, and admits of various modifications that come easy to those skilled in the art. For example, it is possible to replace part or whole of the aforementioned sodium salts with other alkaline metal salts or corresponding alkaline earth metal salts. The optimum values of the pH of the buffer solution used for sample dilution and the concentrations of the respective components may vary depending on the kind of cytokine which is the detection subject, and may also depend on the dilution ratio of the biological fluid sample. Such optimization can be attained within the bounds of the usual condition setting processes by those skilled in the art.

Component (c), or the "second antibody", includes a region bindable to the cytokine so as to capture a desired cytokine in a sandwiching fashion with the first antibody. It is desirable that the first antibody and the second antibody are anti-peptide antibodies which recognize different sites (i.e., different epitopes) of the same cytokine molecule without interfering with each other. Therefore, it is essential that the first antibody and the second antibody make a suitable combination in terms of binding ability with the desired cytokine. For example, suitable combinations can be selected from among multiple lots of polyclonal antibodies which are obtained by immunizing an appropriate animal with the full-length cytokine or a fragment of that cytokine which is known or predicted to include a plurality of epitopes. Alternatively, suitable combinations can be selected from among a plurality of monoclonal antibodies which recognize different epitopes. Such a selection can be achieved without particular difficulties through a preliminary experiment which involves preparing a reference solution of cytokine and performing a usual ELISA method with respect to combinations of antibodies to be considered, for example.

The second antibody may further include a portion to which biotin is bound so as to enable detection of the cytokine through fluorescence measurement. In this sense, the second antibody is also referred to as a "detection antibody". Biotin is a vitamin which is also referred to as vitamin H or coenzyme R, and is capable of forming an amide bond with an amino group such as a peptide. The second antibody can be prepared by biotinating and purifying an antibody to the cytokine which is the detection subject following usual methods. The "portion to which biotin is bound" of the second antibody refers to biotin itself as well as the part of the antibody to which biotin is bound (typically the Fc region). If necessary, biotin and a portion of the antibody may be linked by using a bifunctional linker molecule which is capable of binding to both.

As used herein, the expression "second antibody" does not necessary refer to a single molecule, but may represent any structural unit that fulfills the required functions (i.e., the function of being able to bind to a cytokine through an antigen-antibody reaction or a ligand-receptor bond, and the function of carrying biotin). The same also applies to the aforementioned "first antibody". For example, a combination of an antibody to a desired cytokine and a biotinated anti-IgG antibody which is capable of binding to this anti-cytokine antibody can be employed in the present invention. In this case, the combination of the anti-cytokine antibody and the biotinated anti-IgG antibody is collectively referred to as the "second antibody". A biotinated anti-IgG antibody is convenient because of its versatility. In the case where an antibody to a desired cytokine has resistance against a biotination reaction for some reason, the use of a combination with a biotinated anti-IgG antibody may be useful. On the other hand, from the perspective of simplifying the assay procedure and maximizing the cytokine detection sensitivity, it is preferable to employ a single molecule as the second antibody.

Component (d), or a "conjugate" is any structural unit including streptoavidin or avidin and a fluorescent structural portion capable of being complexed with a lanthanoid metal ion, and is typically a molecule in which streptoavidin or avidin and the fluorescent structural portion are directly or indirectly linked via a covalent bond. Streptoavidin is generally well-known as a protein produced by Actinomycetes and having a molecular weight of about 60,000, and strongly binds to biotin by nature. In the present invention, however, "streptoavidin" is not limited to those of any particular microbial origin, but may include corresponding proteins of any other microbial origin, as well as modifications thereof, so long as its binding ability with biotin is substantially retained. Avidin is generally well-known as a protein having a molecular weight of about 70,000 contained in egg white, and also strongly binds to biotin by nature. In the present invention, "avidin" is not necessarily limited to natural egg white protein, but may include modifications thereof so long as its binding ability with biotin is substantially retained.

As will be seen from the aforementioned principles, the method according to the present invention can also be carried out by employing, instead of component (c), an antibody including a region bindable to a cytokine and a portion to which streptoavidin or avidin is bound; and employing, instead of component (d), a conjugate which includes biotin and a fluorescent structural portion capable of being complexed with a lanthanoid metal ion.

The fluorescent structural portion of the conjugate of component (d) that is capable of being complexed with a lanthanoid metal ion is a partial structure which be obtained by allowing a corresponding fluorescent compound to react so as to be directly or indirectly linked via a covalent bond with streptoavidin or avidin. The fluorescent structural portion is represented by General Formula (I) below:

$$-R-Ar-C(=O)-CH_2-C(=O)-C_nF_{2n}-X \quad (I)$$

(in the formula, R represents a residue which is a functional group capable of forming a covalent bond with a protein; Ar represents a hydrocarbon group having a conjugated double bond system; n is an integer equal to or greater than 1; and X is a fluorine atom or a group represented by General Formula (II):

$$-C(=O)-CH_2-C(=O)-Ar-R \quad (II).$$

In the above general formulae, the "functional group which is capable of forming a covalent bond with a protein", which defines the residue R, refers to any organic functional group that is capable of forming a covalent bond by reacting with any reactive group (typically an amino group, a carboxyl group, and a hydroxyl group) included in an amino acid residue within the protein. Examples of such functional groups include the following groups:

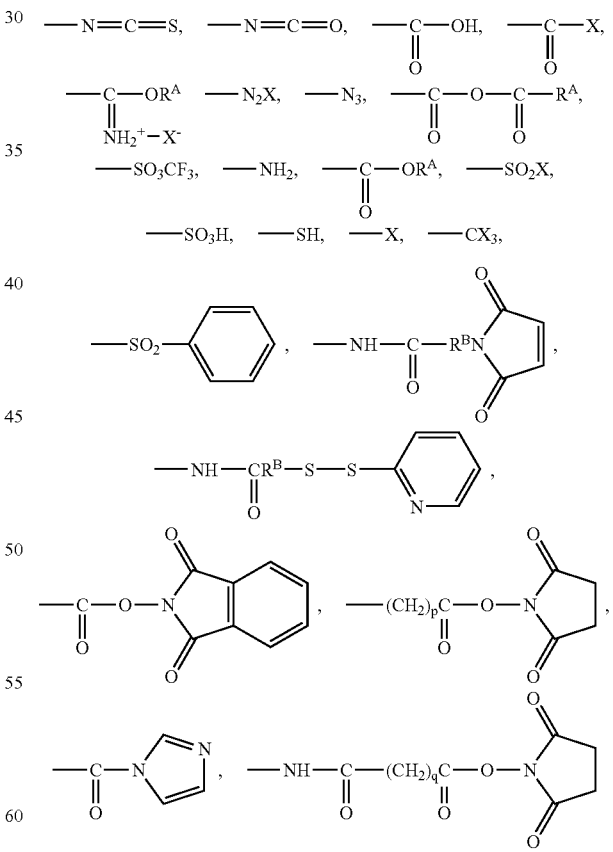

(where X is selected from a halide atom, $-OSO_2CH_3$, $-OSO_2F$, $-OSO_2CF_3$, $-OSO_2C_4F_9$, or $-OSO_2PhCH_3$-p (where Ph represents a phenyl group); $R^4$ is selected from an alkyl group, an alkenyl group, an aryl group, or an aralkyl group; $R^B$ is selected from an alkylene group, an alkenylene group, an arylene group, or an aralkylene group; p is 0 to 5; and q is 2 to 10).

In the above general formulae, the "hydrocarbon group having a conjugated double bond system", which defines Ar, is a hydrocarbon group having at least three conjugated double bonds, and is typically a divalent or trivalent aromatic hydrocarbon group having at least one phenyl ring. The upper limit of the number of carbons in the hydrocarbon group is typically about 50 or less, and preferably about 30 or less, although not particularly limited thereto. Herein, one or more carbon may be substituted by a hetero atom (e.g., an oxygen or sulfur atom). Examples of the hydrocarbon group Ar include the following groups:

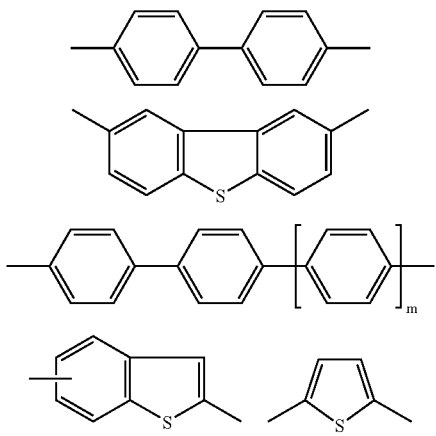

(where m is an integer of 1 to 6)

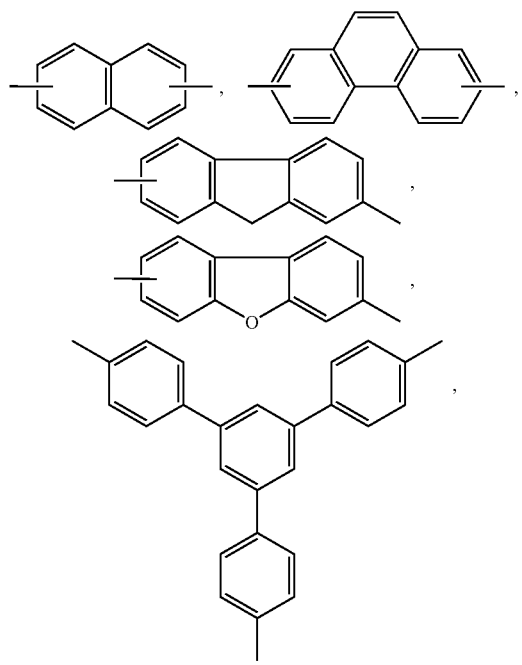

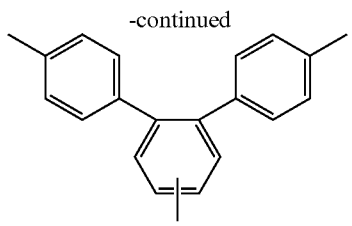

-continued

Preferably, the hydrocarbon group Ar is trivalent, and the fluorescent structural portion is represented by General Formula (III):

—R—Ar—C(=O)—CH$_2$—C(=O)—C$_n$F$_{2n+1}$)$_2$      (III).

Herein, a more preferable example of Ar is o-terphenyl which binds to two β-diketone groups at the 4,4' positions. Another similarly preferable example of Ar is a trivalent aromatic hydrocarbon group which can cause two β-diketone groups to be positioned at similar locations to, or at substantially the same spatial distance as, the locations of the β-diketone groups associated with o-terphenyl.

In the above general formulae, n is an integer of 1 or more, typically 1 to 6, and preferably 2 to 4.

In the present invention, a particularly preferable fluorescent structural portion is 4,4'-bis(1",1",1",2",2",3",3"-heptafluoro-4",6"-hexanedion-6"-yl)-sulpho-o-terphenyl. This is obtained from a corresponding fluorescent compound 4,4'-bis(1",1",1",2",2",3",3"-heptafluoro-4",6"-hexanedion-6"-yl)-chlorosulpho-o-terphenyl (abbreviated as "BHHCT"). The structural diagram of BHHCT is shown below:

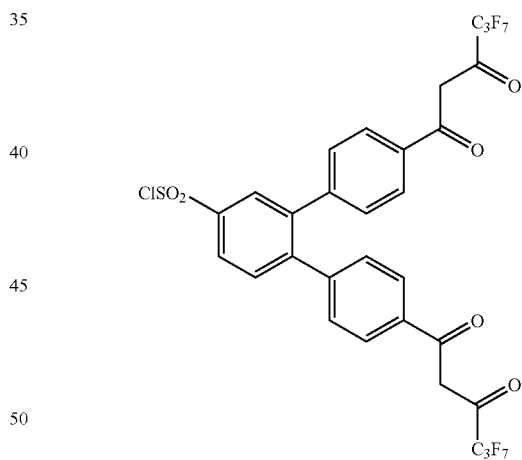

A desired fluorescent compound which gives the aforementioned fluorescent structural portion can be synthesized by utilizing routine organic synthesis reactions. Typically, it can be synthesized by following a procedure consisting of the following two steps:

(First step) A claisen condensation reaction between an acetylated aromatic compound and perfluorocarboxylate ester is carried out in an appropriate solvent in the presence of a basic catalyst (e.g., sodium methylate), thereby producing a β-diketone compound in which the CH$_3$— of an acetyl group has been perfluorocarbonylated.

(Second step) A functional group which is capable of forming a covalent bond with a protein is introduced into the β-diketone compound. For example, hydrogens of the aromatic ring are substituted by chlorosulfonyl groups ($ClSO_2$—) through a chlorosulfonylation reaction using chlorosulfuric acid. After the respective steps, purification such as recrystallization or precipitation can be performed as necessary.

The resultant fluorescent compound is allowed to react with a protein under appropriate conditions, depending on the kind of the functional group which was introduced during the aforementioned second step, thereby giving the fluorescent structural portion of interest. For example, a chlorosulfonyl group easily forms an amide with an amino acid within a protein under basic reaction conditions.

In the present invention, the conjugate of component (d) can be prepared by directly labeling streptoavidin or avidin with a fluorescent compound. Alternatively, the conjugate of component (d) can be prepared by first allowing streptoavidin or avidin to conjugate to another protein (e.g., bovine serum albumin) and then further labeling it. The conjugation between the streptoavidin or avidin and another protein can be achieved following usual methods, e.g., by a cross-linking reaction using glutaraldehyde.

The labeling reaction for the protein with a fluorescent compound can be carried out typically by dissolving the protein in a buffer solution which has been adjusted to an appropriate pH for the reaction (e.g., approximately pH 9 in the case of chlorosulfonylation), and adding thereto a fluorescent compound which has been dissolved in an appropriate solvent (e.g., ethanol or dimethylformamide in such an amount as to achieve a desired molar ratio. By adjusting the molar ratio of the fluorescent compound to the protein and the concentration of the solution containing the fluorescent compound, it is possible to control the ratio (also referred to as the "conjugation ratio") of the fluorescent compound which conjugates to each molecule of the protein. The conjugation ratio corresponds to the number of units of the fluorescent structural portion which are present per molecule of streptoavidin or avidin in the conjugate according to the present invention. The conjugation ratio may typically be 5 to 100 units, and preferably 10 to 60 units. If the conjugation ratio is too small, a sufficiently high cytokine detection sensitivity may not be obtained. On the other hand, too high a conjugation ratio may not make for the improvement in the detection sensitivity.

The composite formation on a solid phase in the method according to the present invention is accomplished as component (e) of a lanthanoid metal ion complexes with the aforementioned fluorescent structural portion. Examples of lanthanoid metal ions include europium (Eu), samarium (Sm), terbium (Tb), and dysprosium (Dy). Europium (Eu) is preferable. The lanthanoid metal ion is previously complexed with the conjugate of component (d) and utilized for the composite formation in that form. In other words, usually the fluorescent structural portion has already become a complex retaining $Eu^{3+}$ at the time when the conjugation with streptoavidin or avidin or biotin is formed. However, this does not exclude the opposite procedure.

The inventors found that it is essential for a high-sensitivity cytokine detection that the composite, which has been thus formed on a solid phase, be adequately washed with an appropriate buffer solution prior to the fluorescence measurement. Herein, an appropriate buffer solution used for washing the composite is an alkaline buffer composed of Tris and inorganic acids, and is typically tris-hydrochloric acid whose pH is typically about 8.2 to about 9.8, preferably about 8.5 to about 9.5, and more preferably about 8.7 to about 9.4, and whose concentration is typically about 0.005 to about 0.2 M, preferably about 0.01 to about 0.1 M, and more preferably about 0.025 to about 0.075 M.

The buffer solution used for washing the composite further contains an appropriate amount of nonionic surfactant having a protein solubilizing ability. The nonionic surfactant is typically polyoxyethylenesorbitan monolaurate, and preferably a polyoxyethylenesorbitan monolaurate which is commercially available under the product name "Tween (registered trademark) 20" (molecular weight: about 1200). Other nonionic surfactants which have substantially the same properties as those of Tween (registered trademark) 20 (e.g., a hydroxy value about 95 to about 115; a saponification value of about 35 to about 55; and an HLB (hydrophilicity-hydrophobicity balance) of about 15 to 18)) can also be preferably used. The concentration of the nonionic surfactant is typically about 0.005 to about 0.2%, preferably about 0.01 to about 0.1%, and more preferably about 0.025 to about 0.075%.

It will be appreciated that the composition of the buffer solution used for washing the composite is not limited to the aforementioned conditions, and various modifications that are easy to those skilled in the art are permitted. The maximum values of pH, the concentrations of the respective components may vary depending on the kind of cytokine to be detected. Such optimization can be achieved within the scope of the usual condition setting process by those skilled in the art.

Hereinafter, a typical example of a procedure for the composite formation on a solid phase according to the method of the present invention will be described.

1) A solution of the first antibody which has been diluted in an appropriate buffer solution used for coating is applied on a solid phase (e.g., in a well of a 96-well microtiter plate), and the first antibody is immobilized on the solid phase through incubation. As the buffer solution used for coating, a phosphate buffer solution containing an appropriate amount of NaCl may be employed, for example. Typically, the incubation conditions are about 2 to 6° C. for about 20 hours or more.

2) Next, the surface of the solid phase which has been coated with the first antibody is washed several times with a buffer solution used for washing. As the buffer solution used for washing, for example, alkalescent tris-hydrochloric acid may be employed, and an appropriate amount of a nonionic surfactant having a protein solubilizing ability may be added as necessary. After washing, the coated solid phase is preserved at a low temperature of about −20° C. until immediately before it is used for an assay.

3) As described above, the biological fluid sample containing a cytokine which is the detection subject is preferably previously diluted to an appropriate level with a buffer solution used for sample dilution. The biological fluid sample, and if necessary a reference solution of the cytokine, is applied to the coated solid phase and incubated. Typically, the incubation conditions are about 35 to 39° C. for about 40 minutes to about 2 hours. After incubation, the surface of the solid phase is washed several times with a buffer solution used for washing, similarly as above.

4) Thereafter, a solution of the second antibody which has been diluted in an appropriate buffer solution is applied to a solid phase and incubated. Herein, it is preferable to employ the same buffer solution used for sample dilution as that described above. The incubation conditions are similar to those in the aforementioned incubation for the biological fluid sample. After incubation, the surface of the solid phase is washed several times with a buffer solution used for washing, similarly as above.

5) The conjugate is mixed with a solution of a salt of a lanthanoid metal ion so as to allow a fluorescent complex portion to be formed. After being diluted in an appropriate solvent, the complexed conjugate is applied to a solid phase and incubated. The incubation conditions are similar to those in the aforementioned incubations for the biological fluid sample and the second antibody. After incubation, the composite which has been formed on the solid phase is washed several times with an appropriate buffer solution used for composite washing, in the aforementioned manner.

Next, the composite containing a lanthanoid complex which has been obtained in the aforementioned manner is subjected to a time-resolved fluorescence measurement in a solid or liquid phase. Apparatuses for this fluorescence measurement are commercially available. Typically, the measurement conditions are: delay time of about 0.2 to about 0.3 milliseconds (ms): a window time of about 0.2 to about 0.6 ms; a flash rate of about 0.5 to about 1.5 ms; an excitation wavelength of 337.1 nm (wavelength of a nitrogen laser); and a measurement wavelength of 615 nm.

In the case of a solid phase fluorescence measurement, the solid phase bearing the aforementioned composite can be subjected to the fluorescence measurement conditions as it is. In the case of a liquid phase fluorescence measurement, the composite is treated with an appropriate dissociation solution to allow any structural units containing the fluorescent complex portion to break free into the solution, and this solution is subjected to the fluorescence measurement conditions. The dissociation is typically a weak-basic aqueous solution containing trialkylphosphinoxide and an anionic surfactant. As an example of a dissociation solution, an aqueous solution of sodium hydrogen carbonate ($NaHCO_3$) containing tri(n-octyl)phosphinoxide (TOPO) and sodium dodecyl sulfate (SDS) may be used. By incubating the solid phase bearing the aforementioned composite at about 45 to 55° C. for about 40 minutes to about 2 hours, the conjugation with the streptoavidin or avidin or biotin is severed, so that the conjugate containing the fluorescent complex portion breaks free into the solution.

The aforementioned liquid phase fluorescence measurement advantage permits a wider range of types of solid phases and materials to be selected because the fluorescence measurement does not involve a solid phase. On the other hand, the liquid phase fluorescence measurement leads to a complicated procedure because of requiring extra steps as compared to the solid phase fluorescence measurement. Furthermore, the liquid phase fluorescence measurement may in some cases provide a somewhat lower sensitivity than that of the solid phase fluorescence measurement for reasons such as susceptibility to the influence of impurities during the step of dissociation solution treatment. However, it will be understood that the respective maximum sensitivities that are achieved by the solid and liquid fluorescence measurements may vary depending on the combination of various conditions concerning the assay.

According to the present invention, a kit for carrying out the aforementioned time-resolved fluoroimmunoassay (TR-FIA) method is further provided. This kit usually includes at least the aforementioned components (a), (c), (d) and (e) as component items. In other words, a first antibody including a portion bound to a solid phase and a region bindable to a cytokine; a second antibody including a region bindable to the cytokine and a portion to which biotin is bound: a conjugate including streptoavidin or avidin and a fluorescent structural portion capable of being complexed with a lanthanoid metal ion; and the lanthanoid metal ion are provided in an integral manner to a measurer, thereby making it possible to perform an assay for detecting the cytokine in a biological fluid sample. As necessary, the kit may further include a reference cytokine, the aforementioned various buffer solutions (in particular a buffer solution used for sample dilution and a buffer solution used for composite washing), and the like. The component items of the kit may usually be accommodated in vessels in their respectively appropriate forms, and packaged in an integral manner along with explanations or instructions for use.

The present invention makes available a novel method which is capable of detecting cytokines accurately and with high sensitivity, especially chemokines including SDF-1, in a biological fluid sample. The detection limit according to the method of the present invention may typically be about 100 pg/ml or less, preferably about 50 pg/ml or less, and more preferably about 30 pg/ml or less, as derived under substantially the same conditions as in Example 2 described below. Similarly, a coefficient of variation (CV) for cytokine measurement may typically be less than about 10%, preferably less than about 8%, and more preferably less than about 7%, as derived under substantially the same conditions as in Example 2 described below. The recovery rate of the cytokine from a plasma sample may typically be about 70% or more, preferably about 80% or more, and more preferably about 90% or more, as derived under substantially the same conditions as in Example 6 described below. Furthermore, the fluctuations in the measured values obtained when measurements are repeated for the cytokine in plasma samples derived from the same individual under the same conditions on four or more different days may preferably be in a range of about 10 to about 20%.

As illustrated in the examples below, by utilizing an $Eu^{3+}$ complex derived from a fluorescent compound BHHCT according to the present invention, the detection sensitivity in plasma samples was improved by two or three orders of magnitude relative to conventional methods such as ELISA and DELFIA, especially with respect to SDF-1. It is highly important to accurately grasp the behavior of SDF-1 in vivo and reveal its physiological functions, in order to deepen the understanding of HIV-1 infections and to open up new prospects of AIDS treatment. It is evident that the present invention can make particularly significant contributions to the development and application of molecular biology concerning cytokines.

Furthermore, as illustrated in the examples below, it has been shown that, by utilizing an $Eu^{3+}$ complex derived from a fluorescent compound BHHCT according to the present invention, measurements for cytokines other than those of the cytokine family, e.g., cytokines which exist in blood circulation as soluble factors and have biological activities in minuscule amounts and which are not only involved in various pathologies but also are already put to therapeutic applications, are possible with as high a sensitivity as that for SDF-1 and also with a good reproducibility.

EXAMPLES

Hereinafter, the present invention will be described in greater detail by way of examples. These examples are not limiting on the present invention.

Hereinafter, the present invention will be described in detail by way of examples. These examples are not limiting on the present invention.

Materials, apparatuses, and measurement conditions used in the examples are described below.

Antibodies: Anti-SDF-1 antiserum was raised by immunizing a rabbit with a multi-antigen peptide (Research Genetics, Alabama, U.S.) including residues 33-45 (RFFESHIARANVK) of human SDF-1β. The antiserum was purified by an affinity column and used. A goat polyclonal antibody to human SDF-1β was purchased from R&D Systems Inc. (Minnesota, U.S.). A human monoclonal antibody to human granulocyte-macrophage-colony stimulating factor (GM-CSF) was purchased from PharMingen (California, U.S.). A monoclonal antibody to human interleukin 2 (IL-2) was purchased from PharMingen (California, U.S.).

Chemokines: Human RANTES, human MIP-1α and β, human MDC, and human fractalkine were purchased from DIACLONE Research (France). Human IL-8 was purchased from ENDOGEN (Massachusetts, U.S.). A commercially available ELISA kit was used for the determination of mouse IL-8 and mouse MCP-1 which were added to plasma. Mouse IL-8 was purchased from Amersham Pharmacia Biotech (Sweden), and mouse MCP-1 was purchased from PharMingen (California, U.S.). Mouse SDF-1α, mouse SDF-1β, human SDF-1α, and human SDF-1β were each donated from Genetics Institute (Massachusetts, U.S.). Human GM-CSF was purchased from PharMingen (California, U.S.). HumanIL-2 was purchased from PharMingen (California, U.S.).

Apparatuses and measurement conditions: 1420 ARVO multi-label counter from Wallac (Finland) and Amersham Pharmacia Biotech (Sweden) was used for time-resolved fluorescence measurement under the following measurement conditions: a delay time of 0.20 milliseconds (ms), a window time of 0.40 ms, and a flash rate of 1.00 ms. In order to obtain a most sensitive TR-FIA assay system, five types of microtiter plates which had been purchased from Nunc (Denmark) were examined, among which a polysorp plate produced the most sensitive fluorescence signals in the measurement of reference human SDF-1β. The order of sensitivity was as follows: White C96 maxisorp>C96 maxisorp>White C8 maxisorp>Black F16 maxisorp. In the following experiments, White C96 polysorp microtiter plates were consistently used.

Example 1

Preliminary Study for TR-FIA

Initially, efforts were made to identify good combinations of solid-phase-bound capture antibodies and detection antibodies which are appropriate for an ELISA-based immunoassay system for SDF-1 measurement. For this purpose, various combinations were studied from a total of five kinds including polyclonal rabbit anti-SDF-1 antibodies and polyclonal goat anti-SDF-1 antibodies. Specific detection of reference SDF-1 was observed in three combinations. However, the detection limit for SDF-1 in the ELISA assay never exceeded about 10 to 20 ng/ml. Usually, the level of SDF-1 present in plasma is much lower than such a detection limit. Thus, it was confirmed that it is virtually impossible to detect SDF-1 in plasma samples with an ELISA assay.

By employing the most preferable combinations of polyclonal antibodies that were found in the aforementioned manner, SDF-1 detection was carried out by modifying the usual TR-FIA conditions as described below.

Example 2

TR-FIA for Reference SDF-1

Four kinds of assay buffer solutions were prepared for TR-FIA: Buffer Solution 1 for coating a 96-well microtiter plate (0.15 M phosphate buffer (PBS) containing 0.14 M NaCl); Buffer Solution 2 for washing plates (0.05 M Tris-HCl containing 0.05% Tween20, pH 7.8); Buffer Solution 3 for washing plates (0.05 M Tris-HCl, pH 7.8); and Buffer Solution 4 for diluting protein solutions (0.05 M Tris-HCl containing 0.2% BSA, 0.1% $NaN_3$, and 0.9% NaCl, pH 7.8).

The synthesis of BHHCT was performed following a method described in Yuan et al. ('98)(Document 5); and the preparation of a streptoavidin-bovine serum albumin (SA-BSA) conjugate and the labeling of the conjugate with BHHCT were performed following a method described in Yuan et al. ('97)(Document 4). A solution of the labeled conjugate was preserved at −20° C., and diluted 100× with the buffer solution below (Buffer Solution 4) immediately before use.

Rabbit polyclonal anti-human SDF-1β antibody or goat polyclonal anti-human SDF-1β antibody was used as a capture antibody. They produced similar results. A solution of the capture antibody (60 μl each), having been diluted to 10 μg/ml with Buffer Solution 1, was incubated in a well of a 96-well microtiter plate at 4° C. for 24 hours. Next, this well was washed twice with Buffer Solution 2, and once with Buffer Solution 3. The plate which has been coated with anti-SDF-1 antibody in the above manner can be preserved for at least one month at −20%.

A reference solution of SDF-1 (50 μl) was pipetted onto the aforementioned coated plate, and incubated at 37° C. for 1 hour. After washing the plate with Buffer Solutions 2 and 3, 50 μl of a solution of biotinated goat polyclonal anti-human SDF-1β antibody (obtained by biotinating the aforementioned goat antibody from R&D System by following usual methods), diluted 1000× with Buffer Solution 4, was incubated in a well at 37° C. for 1 hour. After incubation, the plate was washed twice with Buffer Solution 2, and once with Buffer Solution 3, and 50 μl of a BSA-SA solution (50 μl) labeled with BHHCT-$EU^{3+}$ was incubated in a well at 37° C. for 1 hour. The plate was washed four times with 0.05 M Tris-HCl, pH 9.1 containing 0.05% Tween20. This plate was subjected to a solid fluorescence measurement by using a 1420 ARVO multi-label counter.

Figure 1A:
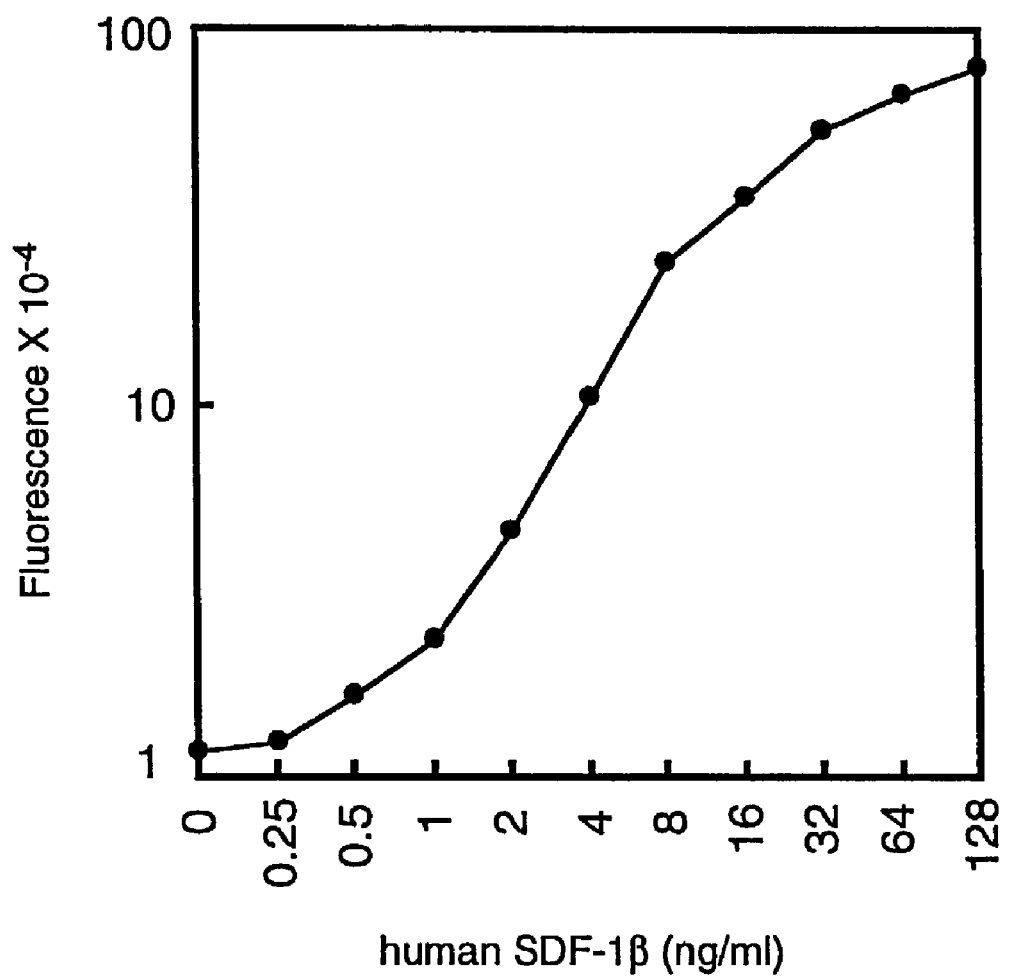
FIG. 1a is a graph illustrating a calibration curve for SDF-1. A reference SDF-1 was measured by using a TR-FIA method described in Example 2. The data indicate average values of triplicate measurements.
Figure 1B:
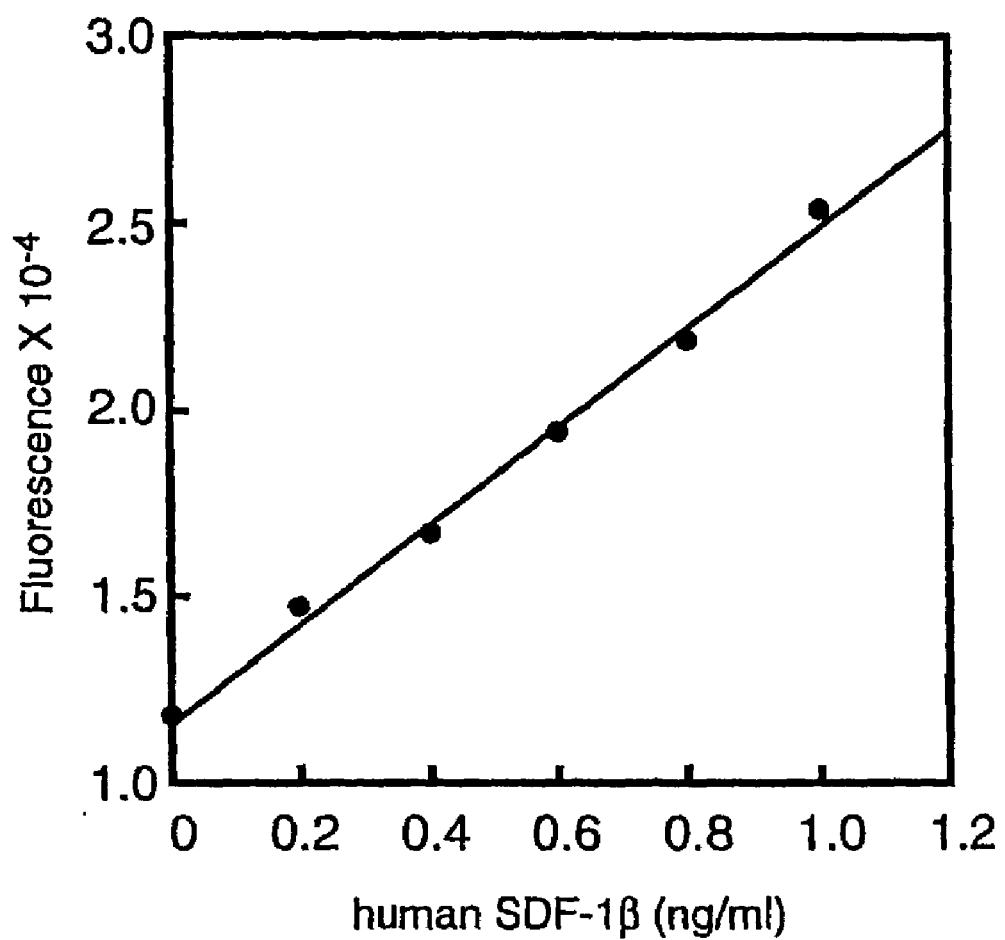
FIG. 1b is a graph illustrating a similar calibration curve as in FIG. 1a with a particular focus on the measurements in a low concentration range. The line in the graph is as follows: Y=1.3X+1.2(×10000 a.u.); r=0.995. The data indicate average values of triplicate measurements.

Calibration curves for the reference SDF-1 within an aqueous solution are shown in FIGS. 1a and 1b. The detection limit for SDF-1 by TR-FIA can be calculated from the following equation (according to Kropf et al. (Document 2):

$3 \times [S_0] \times S_B/(S_0 - B)$, where $[S_0]$ is a minimum concentration of the reference solution;
$S_B$ is a standard deviation of a blank;
$S_0$ is a fluorescence signal intensity of the reference solution at the minimum concentration; and
B is a fluorescence signal intensity of the blank.

From the above equation, the detection limit by TR-FIA was calculated to be 30 pg/ml, which is three orders of magnitude lower than the detection limit (about 10 to 20 ng/ml) by ELISA in the aforementioned referential example. Since 50 μl of the solution is used per well, the minimum amount of SDF-1 protein detectable by TR-FIA is 1.5 pg/well.

TR-FIA was also shown to be improved with respect to measurement reproducibility. The coefficient of variation (CV) for SDF-1 detection by TR-FIA was less than 7% for a reference sample in a concentration range of 0.1 ng/ml to 1024 ng/ml. This is to be contrasted to the fact that the CV value for ELISA in the above-described referential example exceeded 10% in a concentration range of 10 ng/ml to 1000 ng/ml and that CV value for DELFIA (see the Comparative Example below) also exceeded 10% in a concentration range of 0.1 ng/ml to 1024 ng/ml.

In addition to the aforementioned solid phase fluorescence measurement, a liquid phase fluorescence measurement was also studied. Specifically, a fluorescent composite (polyclonal anti-SDF-1 antibody-SDF-1-biotinated polyclonal anti-SDF-1 antibody-BHHCT-$Eu^{3+}$ labeled BSA-SA) formed on a solid phase by the aforementioned procedure was treated with an acidic chelated surfactant solution (a 0.1 M $NaHCO_3$ aqueous solution containing 10 µM TOPO and 0.05% SDS), thereby allowing the labeled BSA-SA conjugate to break free from the solid phase. The fluorescence intensity of the conjugate within the solution was measured by using a 1420 ARVO multi-label counter. The SDF-1 detection sensitivity in this case was about 100 pg/ml, which is not as high as that of the aforementioned solid phase measurement.

Example 3

Down Modulation of CXCR4 by Human SDF-1β

In order to confirm the interrelationship between SDF-1 measurement values by TR-FIA according to Example 2 and the biological activity of the reference SDF-1 protein, an in-vitro down modulation of a SDF-1 receptor (CXCR4) which is induced in EL-4 cells upon binding of SDF-1 was measured.

EL-4 cells were cultured in Dulbecco-modified Eagle's medium (D' MEM), to which 10% fetal calf serum (FCS) was supplemented, under the presence or absence of human SDF-1β (1, 10, 20, 40, 100, and 1000 ng/ml). After 6 hours of incubation at 37° C., the CXCR4 on the cell surface was dyed with Fc-human SDF-1α chimeric protein and FITC-bound goat $F(ab')_2$ anti-human IgG (Southern Biotechnology Associates, Alabama, U.S.). A fluorescence intensity measurement was performed by fluorocytometry (FACS-Calibur, BECTON DICKINSON, California, U.S.). The down modulation of CXCR4 was evaluated by calculating the percentage reduction in the mean fluorescence intensity (MFI) of CXCR4 dyeing. The results are shown in FIG. 1c.

Figure 1C:
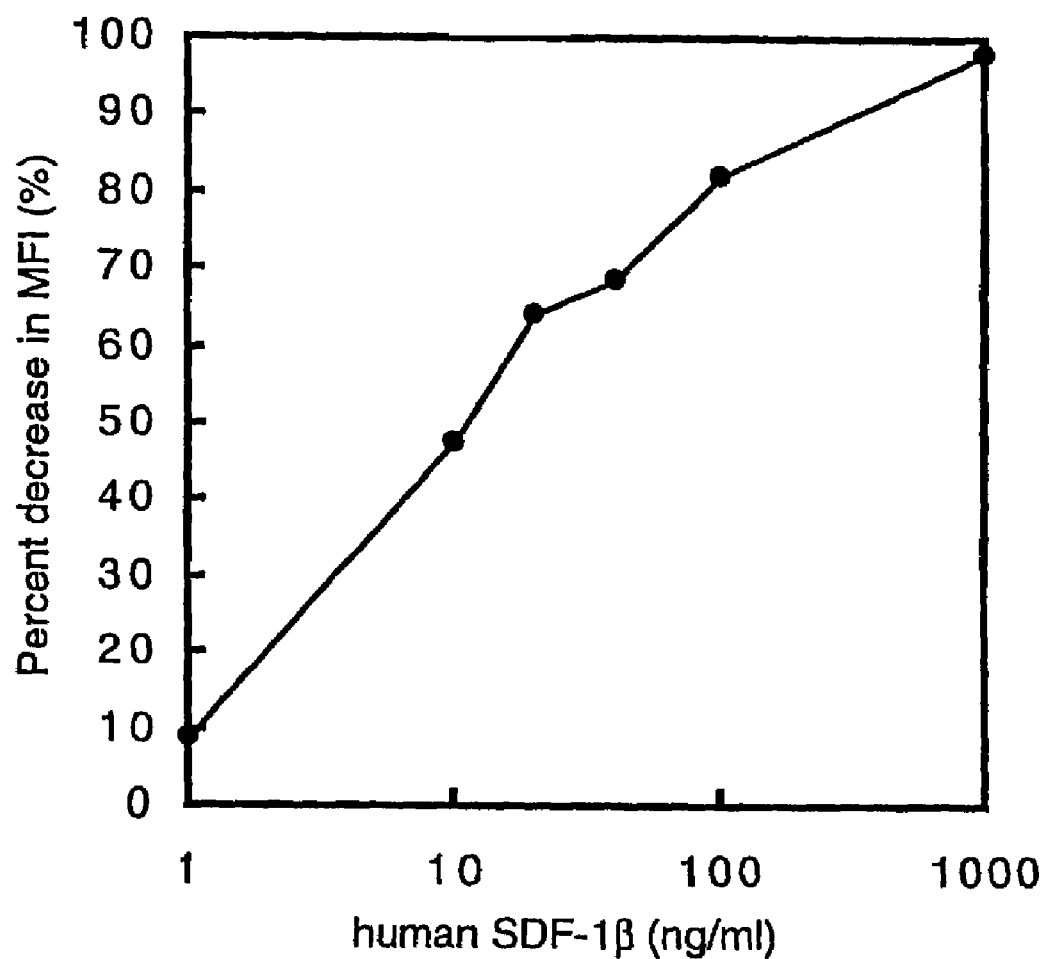
FIG. 1c is a graph illustrating measurement results of CXCR4 expression on the EL-4 cell surface according to a protocol described in Example 3 as a way of monitoring the biological activity of SDF-1. The percentage decrease in a mean fluorescence intensity (MFI) was calculated based on comparison with controls which were incubated without human SDF-1β. The data represent medians selected from three runs of a series of experiments.

From FIG. 1c, it is indicated that EL-4 cells which were cultured with human SDF-1β is down modulated with respect to the CXCR4 expression in a dose-dependent manner. The results obtained were in good agreement with previous reports (Hesselgesser et al. (Document 13) and Amara et al. (Document 14)) that SDF-1α and β bind to CXCR4 with Kd values of 5-10 nM and 2.2-3.6 nM, respectively.

Example 4

Specificity of SDF-1 Measurement by TR-FIA

Figure 1D:
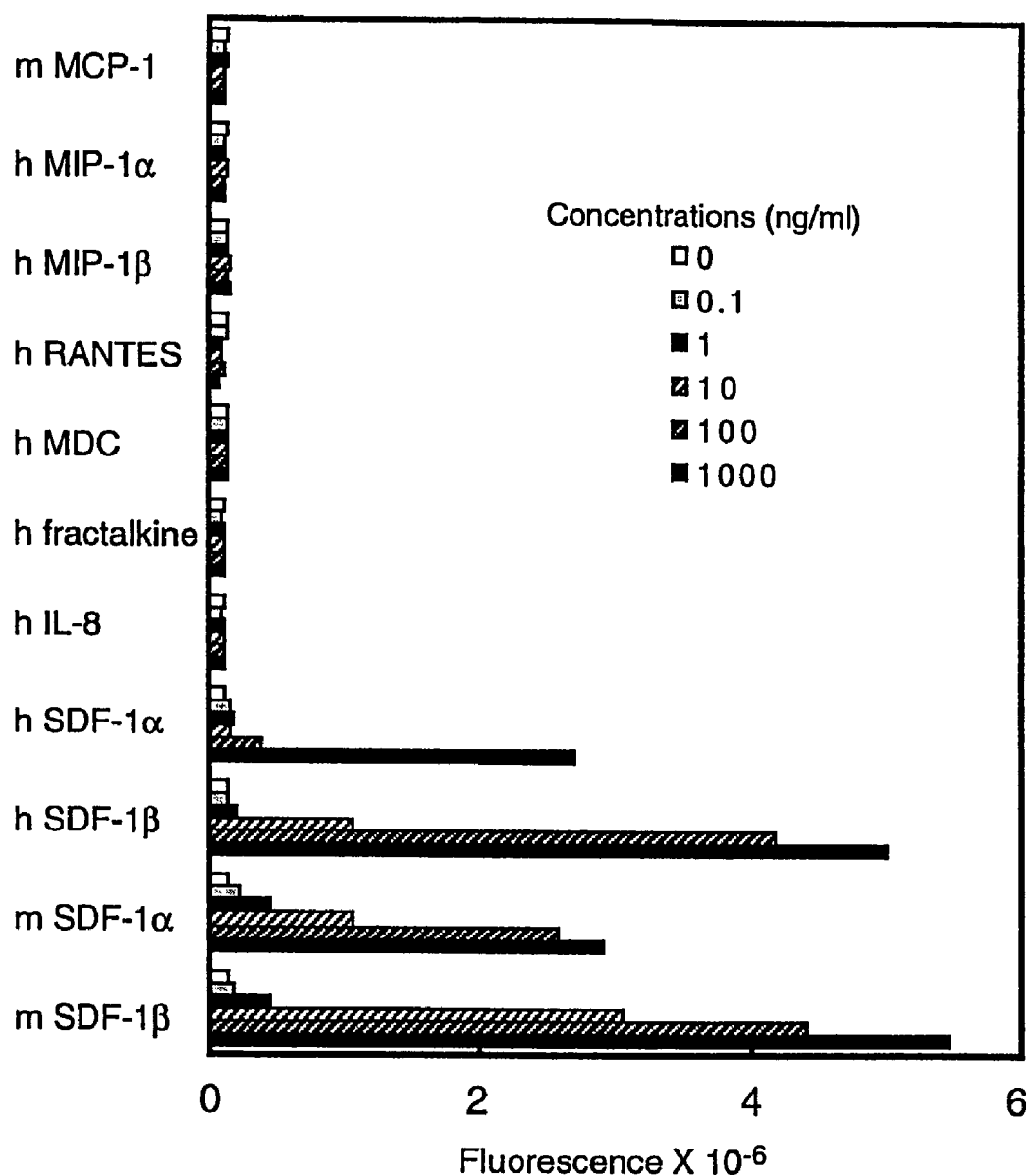
FIG. 1d is a graph illustrating measurement results of various chemokines for evaluating the specificity of TR-FIA with respect to SDF-1. The data indicate average values of triplicate measurements.

In order to confirm the specificity of TR-FIA with respect to SDF-1, TR-FIA measurements similar to those described in Example 2 were taken for the following various chemokines: CC chemokines (mouse MCP-1, human MIP-1α and β, human RANTES, human MDC), CXC chemokines (human IL-8, mouse SDF-1α and mouse SDF-1 β, human SDF-1α and human SDF-1β), and a CXXXC chemokine (human fractalkine). The results are shown in FIG. 1d. No significant increase in the fluorescence intensity was observed in any chemokines other than SDF-1. Thus, it was confirmed that the aforementioned TR-FIA is capable of detecting SDF-1 with a high specificity. Cross-reactivity was exhibited between human and mouse SDF-1α and SDF-1β.

Example 5

Preparation of Plasma Sample

The plasma samples used in the following Examples were prepared from the blood of 36 healthy volunteers (Japanese) aged between 18 to 30, by using EDTA (1 mg/ml of blood) as an anticoagulant. Specifically, PBS containing 0.5 M EDTA was filled in a syringe coated with 0.1 M EDTA so that 7 µl of it would be present for every 1 ml of the collected blood. Blood was collected into this syringe, incubated at room temperature for 5 minutes, and then centrifuged at 3000 rpm for 10 minutes, thereby obtaining plasma. The plasma samples were preserved at −80° C., and diluted 10× with Buffer Solution 4 immediately before use, unless otherwise specified. It was ensured that freezing/thawing would not be repeated before the assay.

Example 6

TR-FIA for Plasma Samples

The TR-FIA as described in Example 2 was performed for the reference SDF-1 solution and the aforementioned plasma samples (obtained from five individuals). The SDF-1 concentration in each plasma sample was calculated by comparison against a calibration curve (,i.e., a line graph depicted with black circles on the left-hand side of FIG. 2) which was derived from measurements of the reference solution. Furthermore; in order to confirm the accuracy of the measurements, a measurement was performed by adding 0.4 or 0.8 ng/ml of reference SDF-1 to each plasma sample, and the recovery rates were calculated.

Figure 2:
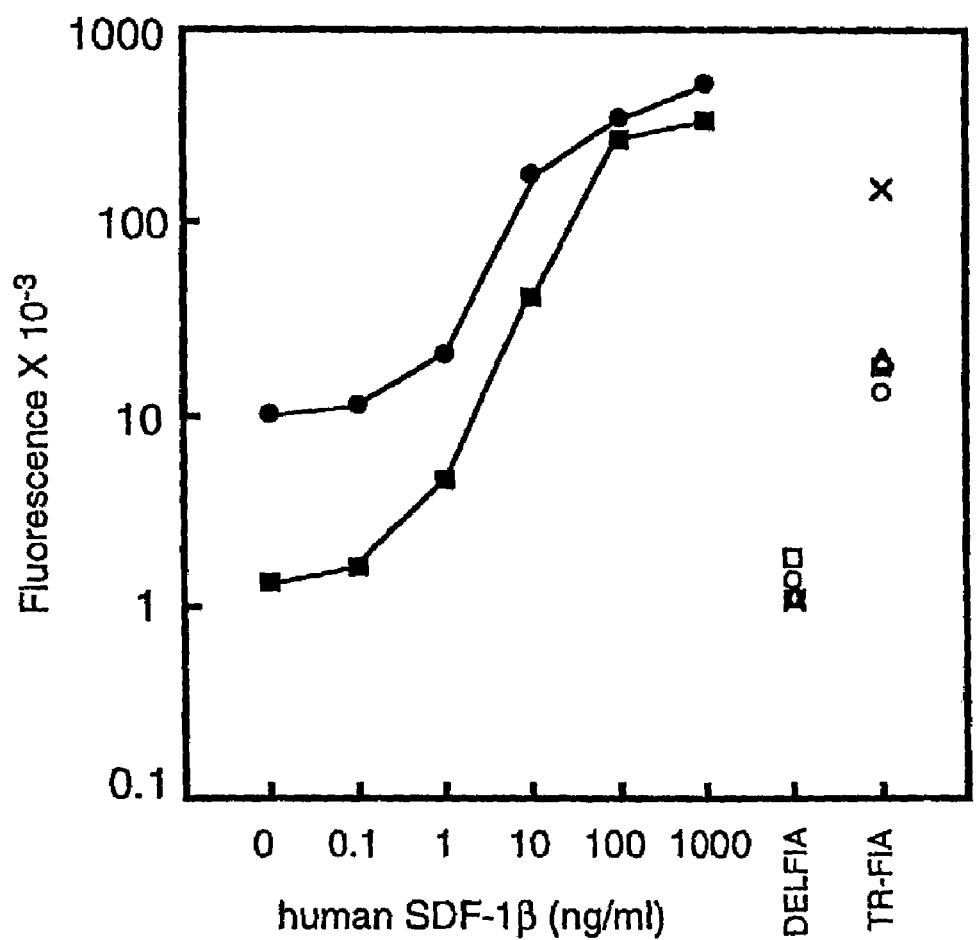
FIG. 2 is a graph illustrating a comparison between TR-FIA and DELFIA with respect to SDF-1. On the left-hand side of FIG. 2 are shown measurement results of a reference solution of human SDF-1β by DELFIA and TR-FIA systems by employing the same combinations of a capture antibody and a detection antibody as those employed in Example 2. On the right-hand side of FIG. 2 are shown results of endogenous SDF-1 concentrations within plasma samples as obtained by the two systems. The samples shown on the right-hand side of FIG. 2 have no reference SDF-1 added thereto. The data on the right-hand side of FIG. 2 and the data shown in Table 1 represent measurement results for different samples. The data indicate average values of triplicate measurements.

The measured fluorescence intensities for the plasma samples having the reference SDF-1 added thereto are shown on the right-hand side of FIG. 2 (under the caption "TR-FIA"). The SDF-1 concentrations and recovery rates of the plasma samples before and after the addition of the reference SDF-1 are shown in Table 1 below. It was indicated that TR-FIA makes it possible to detect SDF-1 in plasma samples as in the case of the reference solution, with high recovery rates.

Comparative Example

DELFIA for SDF-1

The following measurement operations of DELFIA were performed in accordance with the instructions provided by the manufacturer (Amersham Pharmacia Biotech; hereinafter "APB"), unless otherwise specified. All washings were done by using PBS/0.05% Tween20.

A solution of rabbit anti-human SDF-1β antibody or goat anti-human SDF-1β antibody (60 µl each), having been diluted down to 10 µg/ml with PBS, was adsorbed to a transparent maxisorp plate (Nunc, Denmark), incubated at 4° C. for 24 hours, and thereafter washed once. Next, in order to block non-specific binding, 180 µl of a DELFIA assay buffer solution (APB) was applied at room temperature for at least 30 minutes.

After the plate was washed three times, reference SDF-1 diluted with the DELFIA assay buffer solution, or 10× diluted plasma samples were added in an amount of 50 μl per well, and incubated at 4° C. for at least 6 hours. After the plate was washed three times, 100 μl of Eu labeled streptoavidin (APB), having been diluted down to 20 ng/ml, was added in the assay buffer solution, and incubated at room temperature for 30 minutes. After the plate was washed six times, a DELFIA sensitizing solution (APG) was added so as to allow $Eu^{3+}$ to dissociate from the Eu-labeled antibody bound to the solid phase. After slowly shaking the microplate for 5 minutes, the fluorescence was measured with a time-resolved fluorometer (ARVO 1420).

A calibration curve derived from measurements of the reference solution is shown on the left-hand side of FIG. 2 (i.e., a line graph depicted with black squares). The detection limit which was calculated in accordance with the equation described in Example 2 be 130 pg/ml. DELFIA was able to detect SDF-1 in the reference solution, although with a lower sensitivity than by TR-FIA. However, none of the measurements of the plasma samples (from four individuals) successfully detected endogenous SDF-1. Furthermore, the recovery rates in the measurements which were taken by adding 1.0 ng/ml of reference SDF-1 to each plasma sample were about 20% or less, which is much lower than those associated with TR-FIA.

The fluorescence intensities which were measured for the plasma samples to which the reference SDF-1 was added are shown on the right-hand side of FIG. 2 (under the caption "DELFIA"). The SDF-1 concentrations and recovery rates of the plasma samples before and after the addition of the reference SDF-1 are shown in Table 1. (It should be noted that the plasma samples illustrated in FIG. 2 and the data of Table 1 were all subjected to preliminary heating at 55° C. for 30 minutes).

TABLE 1

Recovery rate of SDF-1 added to human plasma

| reference added | SDF-1 (ng/ml) | SDF-1 measurements (ng/ml) | expected total SDF-1 (ng/ml) | recovery rate (%) |
| --- | --- | --- | --- | --- |
| (a) TR-FIA | 0 | 1.08 | — | |
| | 1.0 | 2.10 | 2.08 | 102 |
| | 0 | 1.53 | — | |
| | 1.0 | 2.48 | 2.53 | 95 |
| | 0 | 1.68 | — | |
| | 1.0 | 2.69 | 2.68 | 101 |
| | 0 | 1.87 | — | |
| | 1.0 | 2.83 | 2.87 | 96 |
| | 0 | 2.14 | — | |
| | 1.0 | 3.11 | 3.14 | 97 |
| (b) DELFIA | 0 | <D.L. | | |
| | 1.0 | 0.20 | >1.0 | <20 |
| | 0 | <D.L. | | |
| | 1.0 | 0.16 | >1.0 | <16 |
| | 0 | <D.L. | | |
| | 1.0 | 0.17 | >1.0 | <17 |
| | 0 | <D.L. | | |
| | 1.0 | 0.20 | >1.0 | <20 |

<D.L.: below detection limit (130 pg/ml)

Example 7

Influences of Anticoagulants and Protease Inhibitors

Anticoagulants and protease inhibitors are reported to affect measurement of cytokines in human plasma samples (Thavasu et al. (Document 15)). The following experiments were conducted in order to study whether or not the SDF-1 measurement by TR-FIA is affected by such factors.

Figure 3A:
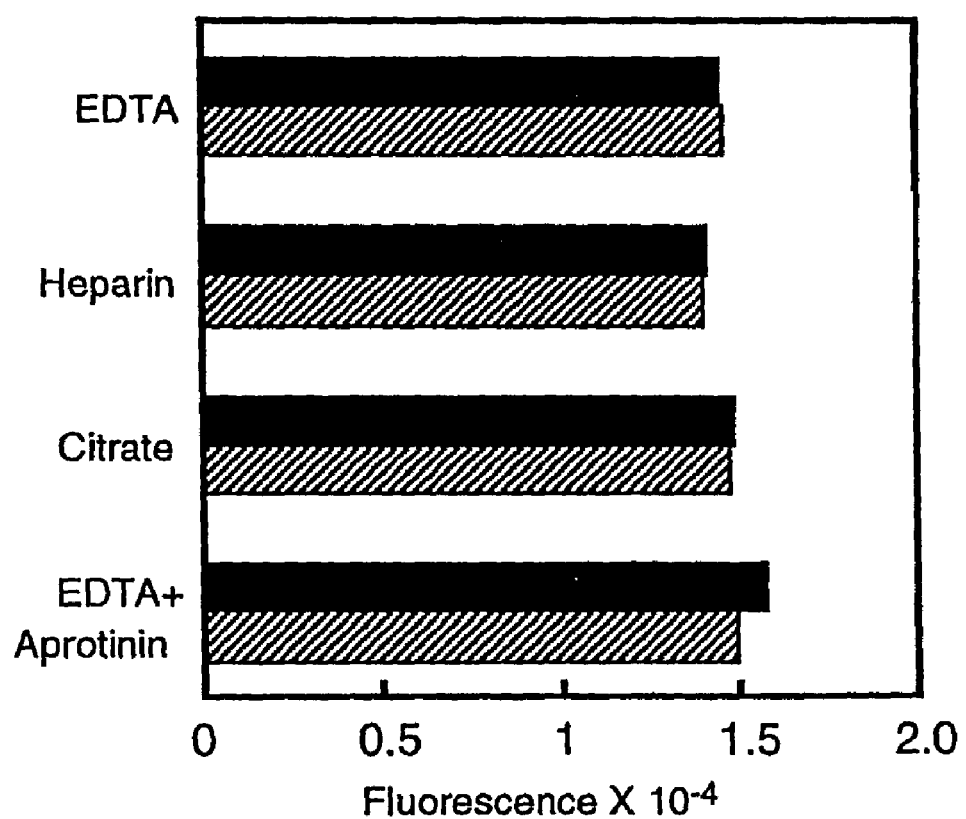
FIG. 3a is a graph illustrating the influences of anticoagulants and protease inhibitors on the SDF-1 measurement by TR-FIA. Plasma samples were treated with EDTA (1 mg/ml); heparin (30 IU/ml); a citrate (sodium citrate 0.38%); or EDTA (1 mg/ml) containing aprotinin (1 μg/ml). The block bars and the hatched bars represent measurement results for two different samples. The data indicate average values of triplicate measurements.

Ethylenediamine tetraacetic acid (EDTA) (1.0 mg/ml), heparin (30 IU/ml), sodium citrate (0.38%), or ethylenediamine tetraacetic acid (EDTA) (1.0 mg/ml) and aprotinin (1 μg/ml), which is a protease inhibitor, was added to plasma samples. In a manner similar to Example 2, SDF-1 was measured by TR-FIA for each sample with additions. The results are shown in FIG. 3*a*. It was confirmed that anticoagulants and protease inhibitors do not significantly affect the plasma SDF-1 measurements by TR-FIA.

Example 8

Influences of Preliminary Heating of Plasma Samples

In clinical applications of SDF-1 measurement by TR-FIA, it would be necessary to inactivate HIV viruses which may exist in blood-originated samples. Accordingly, the influences of preliminary heating of plasma samples on TR-FIA were studied.

First, in order to examine the thermal stability of SDF-1 protein, SDF-1 reference solutions were kept at 0° C. for 30 minutes; 37° C. for 30 minutes; 55° C. for 30 minutes; 70° C. for 30 minutes; or 100° C. for 1 minute, and thereafter subjected to an assay. Under the conditions of 70° C. for 30 minutes and 100° C. for 1 minute, a decrease in the detected amount was observed which was presumably due to the thermal denaturation of SDF-1. On the other hand, heating at 37 or 55° C. for 30 minutes yielded substantially the same calibration curve as those of the non-heated samples, and did not affect the detected amount of SDF-1.

Figure 3B:
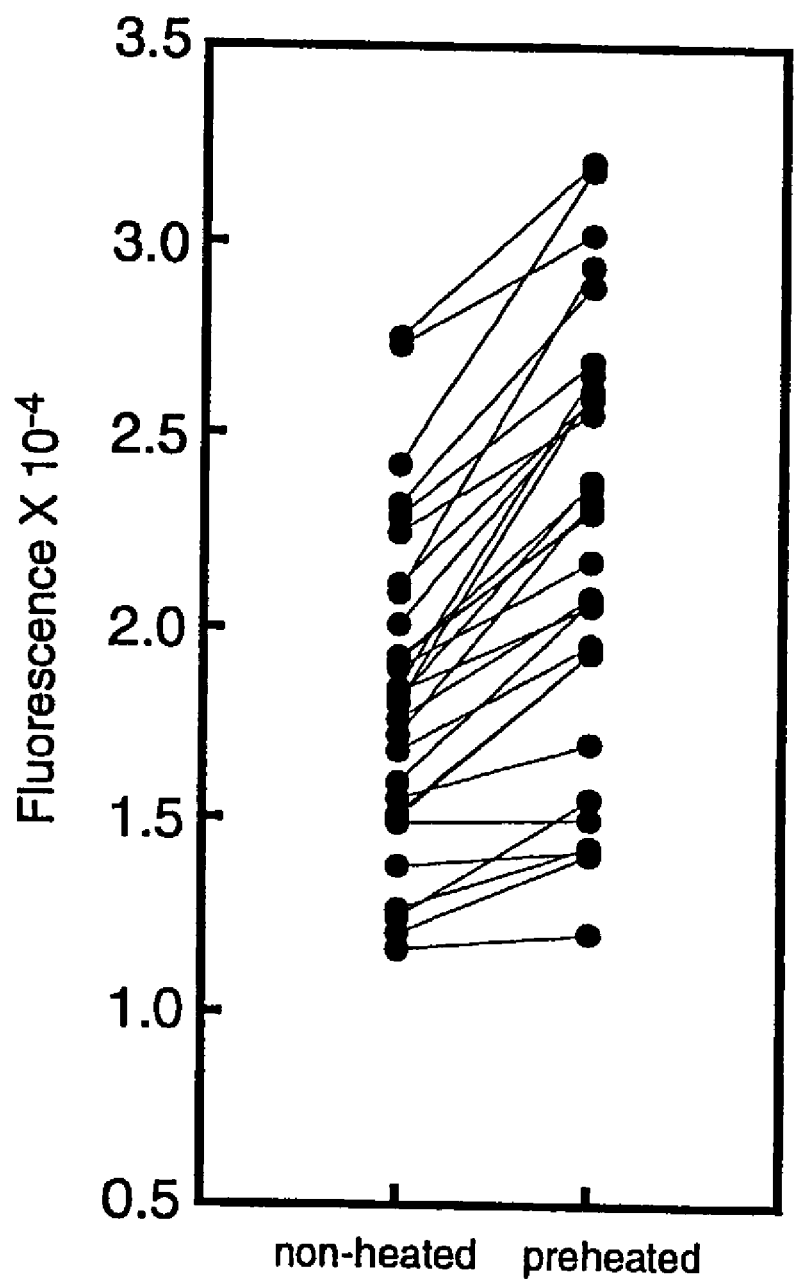
FIG. 3b is a graph illustrating influences of preliminary heating of plasma samples on the SDF-1 measurement by TR-FIA. Plasma samples were previously incubated at 55° C. for 30 minutes before the assay, or directly used for measurement without any heating. The plasma samples were obtained from 24 healthy Japanese volunteers. The data indicate average values of duplicate measurements.

Based on the above results, plasma samples from 24 individuals (see Example 5) were used, with a previous incubation at 55° C. for 30 minutes before the assay or without any heating, in order to measure SDF-1 by TR-FIA in a manner similar to Example 2. (The preliminary heating was performed before diluting the plasma samples with Buffer Solution 4). The results are shown in FIG. 3*b*. The preliminary heating at 55° C. for 30 minutes resulted in an average enhancement in fluorescence intensity of about 20%.

These results suggest the possibility that at least a portion of the SDF-1 in the plasma samples may exist in the form of multimers and/or in a bound form to a binding factor which is thermally dissociated, decomposed, etc. It is possible that the SDF-1 which exists in such multimer and/or bound forms may be inhibited from binding to an epitope.

Example 9

Influence of Dilution of Plasma Samples

Previous work concerning measurement of IL-8 and MCP-1 in plasma samples (Thavasu et al. (Document 15) and Kajikawa et al. (Document 16)) has shown that the amount of chemokines present is underestimated in measurements of non-diluted samples. Accordingly, we studied the influences of dilution of plasma samples on the SDF-1 measurement by TR-FIA.

Figure 3C:
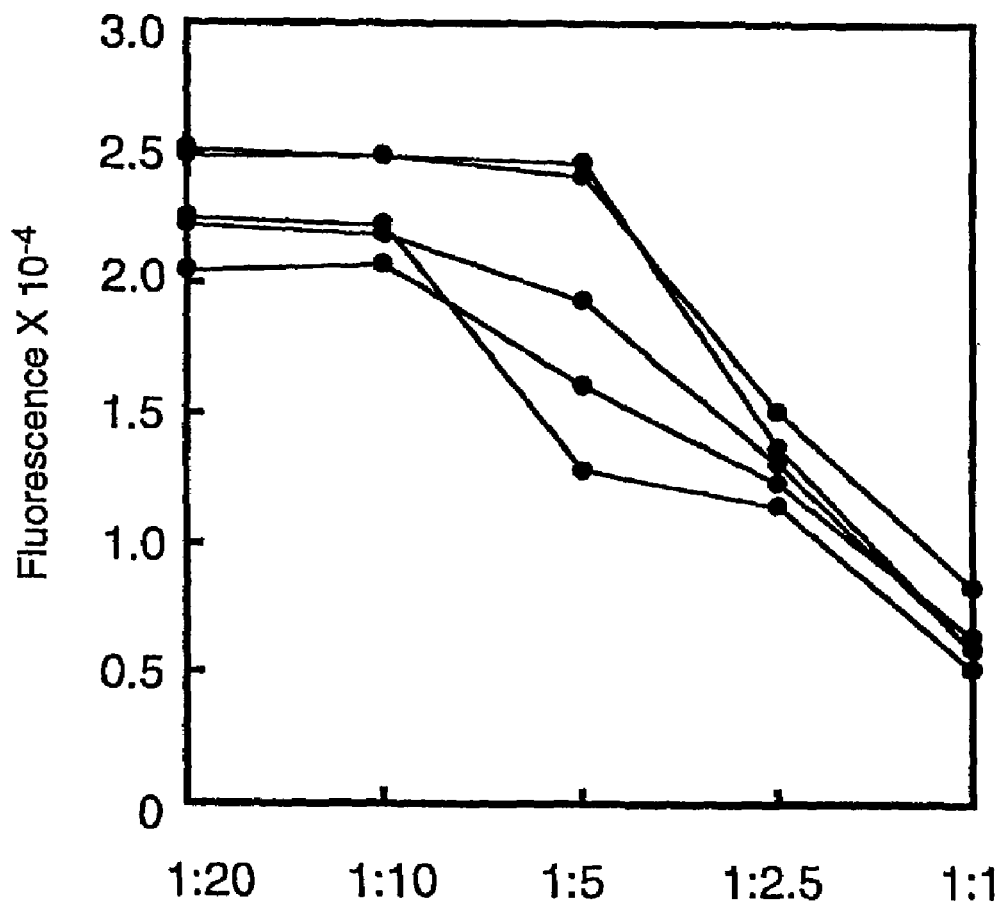
FIG. 3c is a graph illustrating influences of plasma sample dilution on the SDF-1 measurement by TR-FIA. Each sample was diluted in Buffer Solution 4. The plasma samples were obtained from 5 healthy Japanese volunteers. The data indicate average values of triplicate measurements.

Plasma samples from 5 individuals, diluted in Buffer Solution 4 at various ratios from 1:1 to 1:20, were used to measure SDF-1 by TR-FIA in a manner similar to Example 2. The results are shown in FIG. 3*c*. A substantially consistent improvement in detection sensitivity was observed while the dilution ratio was increased from 1× to 10×. On the

Example 10

Influences of Addition of Blood Cells to Plasma Samples

It has been reported that addition of IL-8 and MCP-1 to whole blood results in these chemokines being absorbed by the blood cells (Amara et al. (Document 14), Darbonne et al. (Document 17), and Neote et al. (Document 18)). We studied whether or not similar absorption by blood cells would be observed for SDF-1.

By subjecting 250 μl of whole blood to a microcentrifuge so as to allow the cells to deposit, plasma was obtained as a 125 μl supernatant fraction. IL-8, MCP-1 or SDF-1 was added to the 125 μl of plasma so that a predetermined final concentration was attained. Next, the plasma in which these chemokines were added were mixed with cell pellets which were 125 μl in volume, or with 125 μl of plasma, and thereafter incubated at 37° C. for 15 minutes. Next, as for the samples in which cell pellets were mixed, cells were allowed to deposit through centrifugation and isolated. The soluble IL-8 and MCP-1 within the samples were quantified by ELISA, and the SDF-1 was quantified by TR-FIA. The results are shown in FIGS. 4a to 4c.

Most of the added IL-8 and MCP-1 were absorbed by the blood cells (FIGS. 4a and 4b). On the other hand, the reduction in SDF-1 after incubation with blood cells was less than 10% (FIG. 4c). In another experiment, SDF-1 was directly added to whole blood; after incubation, blood cells were isolated; and thereafter a TR-FIA quantification was carried out, which showed no significant difference from controls obtained by adding SDF-1 to plasma (the data are not shown). From the above, it was confirmed that SDF-1 is scarcely absorbed by blood cells.

Example 11

TR-FIA in Plasma Samples—Multiple Detection

For plasma samples from 36 individuals, SDF-1 was measured by TR-FIA in a manner similar to Example 2, after a preliminary heating at 55° C. for 30 minutes (see Example 7). The results are shown in FIG. 5c. The SDF-1 level in human plasma had a mean value and a standard deviation of 0.85±0.26 ng/ml.

Measurements were repeatedly taken for plasma samples from the same (three) individuals, under the same conditions on four or more different days, whereby the measurement values showed fluctuations within 10 to 20%. It was shown that the plasma SDF-1 measurement by TR-FIA has a sufficiently high reliability.

Example 12

Association of SDF-1 with IgG in Plasma Samples

As for IL-8 and MCP-1, possibilities of binding or association with autoantibodies within the circulatory system are reported as another factor that may hinder immunoassays for plasma samples (Leonard et al. (Document 1) and Thavasu et al. (Document 15)). In the following manner, SDF-1 was evaluated with respect to association with IgG in plasma.

Plasma samples from 7 individuals, without heating or after a heat treatment (55° C., 30 minutes), were incubated on ice with protein G-sepharose for 30 minutes, thereby depleting IgG. The samples were centrifuged, and supernatant fractions were taken therefrom. The SDF-1 in the supernatant was measured by TR-FIA. The rate of decrease in fluorescence intensity relative to the measurement values for the plasma samples before the protein G-sepharose treatment was calculated. The results are shown in FIG. 6.

In FIG. 6, hatched bars and black bars represent unheated samples and heated samples, respectively. It can be seen that the unheated samples are more susceptible to influences of the protein G-sepharose treatment than the heated samples. In the unheated samples, the SDF-1 level that is measurable by TR-FIA decreased by 23 to 37% (an average of 30%) due to depletion of IgG. On the other hand, the corresponding decrease for the heated samples was 6 to 22% (an average of 15%). Thus, the effects of preliminary heating (FIG. 3b) shown in Example 8 can be explained by the hypothesis that a portion of the SDF-1 in plasma samples exists in an associated form with IgG, which is dissociated through heating so as to be converted into a soluble form that is measurable by TR-FIA.

In another experiment, no significant decrease was observed for reference SDF-1 which was added to the plasma samples even after a protein G-sepharose treatment (the data are not shown). Thus, the possibility of SDF-1 itself being adsorbed to protein G-sepharose, and the possibility of antibodies or proteins other than anti-SDF-1 IgG in the plasma samples being adsorbed to protein G-sepharose and the SDF-1 being adsorbed to such antibodies or proteins have been denied.

From the above results, it can be understood that the SDF-1 level in human plasma that is measurable by TR-FIA is very close to the physiological SDF-1 level that is actually present in blood.

Example 13

TR-FIA for GM-CSF

A reference solution of GM-CSF (50 μl) was subjected to a solid phase fluorescence measurement in a manner similar to Example 2, except for using anti-human GM-CSF monoclonal antibody as a capture antibody, and using biotinated anti-human GM-CSF monoclonal antibody (obtained by biotinating the aforementioned PharMingen human antibody by following usual methods), and a calibration curve for the reference GM-CSF was produced. The results are shown in FIG. 7. Furthermore, plasma samples were prepared from healthy Japanese volunteers by a method similar to that of Example 5, diluted in Buffer Solution 4 as described in Example 9, and subjected to a GM-CSF measurement by TR-FIA in a manner similar to that for the reference solution. As a result, a highly sensitive measurement was possible for GM-CSF as well, and excellent results were confirmed as far as reproducibility.

Example 14

TR-FIA for IL-2

A reference solution of IL-2 (50 μl) was subjected to a solid phase fluorescence measurement in a manner similar to Example 2, except for using anti-human IL-2 monoclonal antibody as a capture antibody, and using biotinated anti-human IL-2 monoclonal antibody (obtained by biotinating the aforementioned PharMingen human antibody by following usual methods), and a calibration curve for the reference IL-2 was produced. The results are shown in FIG. 8. Furthermore, plasma samples were prepared from healthy Japanese volunteers by a method similar to that of Example 5, diluted in Buffer Solution 4 as described in Example 9, and subjected to a IL-2 measurement by TR-FIA in a manner similar to that for the reference solution. As a result, a highly sensitive measurement was possible for IL-2 as well, and excellent results were confirmed as far as reproducibility.

INDUSTRIAL APPLICABILITY

A time-resolved fluoroimmunoassay (TR-FIA) method which is capable of detecting cytokines, in particular chemokines including SDF-1, in a biological fluid sample with a very high sensitivity and ease of use is provided, as well as a kit for the method. The method and kit are applicable to cytokines which exist as soluble factors in blood circulation, have a biological activity in minuscule amounts, and are involved in various pathologies.

BIBLIOGRAPHY

1. Leonard, E. J. et al., (1996) METHODS 10:150-157.
2. Kropf, J. et al., (1991) Anal. Biochem. 197:258-265.
3. Ogata, A. et al., (1992) J. Immunol. Methods 148:15-22.
4. Yuan, J. et al., (1997) Anal. Biochem 254(2): 283-287.
5. Yuan, J. et al., (1998) Anal. Chem 70(3):596-601.
6. Tashiro, K. et al., (1993) Science 26:600-603.
7. Bleul, C. C. et al., (1996) Nature 382:635-638.
8. Oberlin, E. et al., (1996) Nature 382:829-833.
9. Winkler, C. et al., (1998) Science 279:389-393.
10. Martin, M. P. et al., (1998) Science 282:1907-1911.
11. Zou, Y-R. et al., (1998) Nature 393:595-599.
12. Tachibana, K. et al., (1998) Nature 393:591-594.
13. Hesselgesser, J. et al., (1998) J. Immunol. 160:877-883.
14. Amara, A. et al., (1997) J. Exp. Med., 186:139-146.
15. Thavasu, P. W. et al., (1992) J. Immunol. Methods 153:115-124.
16. Kajikawa, O. et al., (1996) J. Immunol. Methods 197: 19-29.
17. Darbonne, W. C. et al., (1991) J. Clin. Invest. 88:1362-1369.
18. Neote, K. (1994) Blood 84:44-52.

The invention claimed is:

1. A time-resolved fluoroimmunoassay (TR-FIA) method for detecting a cytokine in a biological fluid sample, comprising:
   subjecting the biological fluid sample to a heat treatment under non-denaturing temperature conditions of about 55° C. for the cytokine;
   forming a composite by (a) binding a first antibody, including a portion bound to a solid phase and a region bindable to a cytokine, to a solid phase; (b) adding the sample containing the cytokine; (c) binding a second antibody, including a region bindable to the cytokine and a portion to which biotin is bound, to the cytokine; (d) adding a conjugate including streptoavidin or avidin and a fluorescent structural portion capable of being complexed with a lanthanoid metal ion; and (e) adding a lanthanoid metal ion to bind the conjugate of (d), the composite being formed on the solid phase; and
   measuring fluorescence of the fluorescent structural portion which has been complexed with the lanthanoid metal ion,
   wherein the method comprises a step of washing after each of steps (a) to (c); and
   wherein the cytokine is a cytokine belonging to the chemokine family, and
   wherein the fluorescent structural portion is represented by General Formula (I):

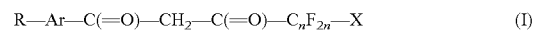

(where R is a residue which is a functional group capable of forming a covalent bond with a protein; Ar is a hydrocarbon group having a conjugated double bond system; n is an integer equal to or greater than 1; and X is a fluorine atom or a group represented by General Formula (II):

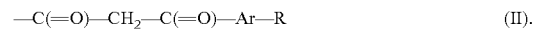

2. The method according to claim 1, wherein the lanthanoid 1 metal ion is europium.
3. The method according to claim 1, wherein the fluorescent structural portion is represented by General Formula (III):

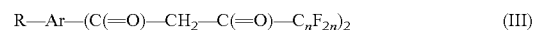

(where R, Ar, and n have the same definitions as in claim 1).
4. The method according to claim 3, wherein the fluorescent structural portion is 4,4'-bis(1", 1",1", 2", 2", 3", 3"heptafluoro-4", 6"-hexanedion-6"-yl)-sulpho-oterphenyl.
5. The method according to claim 1, wherein 10 to 60 units of the fluorescent structural portion are present per molecule of streptoavidin or avidin in the conjugate.
6. The method according to claim 1, wherein the step of measuring fluorescence is performed without allowing the composite formed on the solid phase to dissociate.
7. The method according to claim 1, wherein the step of measuring fluorescence is performed after allowing the composite formed on the solid phase to dissociate.
8. The method according to claim 1, wherein the cytokine is a CXC chemokine.
9. The method according to claim 8, wherein the cytokine is stromal cell-derived factor-1 (SDF-1).
10. The method according to claim 1, wherein the biological fluid sample is plasma or whole blood.
11. The method according to claim 1, further comprising, before the step of forming the composite, a step of diluting the biological fluid sample with a buffer solution used for sample dilution,
   wherein the buffer solution used for sample dilution is 0.01 to 0.1 M tris-hydrochloric acid whose pH is 7.3 to about 8.3, the buffer solution containing 0.1 to 0.3% of bovine serum albumin, 0.05 to 0.2% of sodium azide, and 0.5 to 1.5% of sodium chloride.
12. The method according to claim 1, further comprising, before the step of measuring fluorescence, a step of washing the composite formed on the solid phase with a buffer solution used for washing,
   wherein the buffer solution used for washing the composite is 0.01 to 0.1 M tris-hydrochloric acid whose pH is 8.5 to about 9.5, the buffer solution containing 0.01 to 0.1% polyoxyethylenesorbitan monolaurate.
13. The method according to claim 1, wherein the solid phase is a microtiter plate having an IgG adsorption ability of 50 to 200 ng/cm$^2$.
14. A kit for a time-resolved fluoroimmunoassay (TR-FIA) method for detecting a cytokine in a biological fluid sample, which has been subjected to heat treatment under non-denaturing temperature conditions for the cytokine of about 55° C., comprising: a reference cytokine which has been subjected to heat treatment under non-denaturing temperature conditions for the cytokine of about 55° C.; a first antibody including a portion bound to a solid phase and a region bindable to the cytokine; a second antibody including a region bindable to the cytokine and a portion to which biotin is bound; a conjugate including streptoavidin or avidin and a fluorescent structural portion capable of being complexed with a lanthanoid metal ion; and the lanthanoid metal ion, wherein the cytokine is a cytokine belonging to the chemokine family, and wherein the fluorescent structural portion is represented by General Formula (I):

$$R\text{—}Ar\text{—}C(=O)\text{—}CH_2\text{—}C(=O)\text{—}C_2F_{2n}\text{—}X \qquad (I)$$

(where R is a residue which is a functional group capable of forming a covalent bond with a protein; Ar is a hydrocarbon group having a conjugated double bond system; n is an integer equal to or greater than 1; and X is a fluorine atom or a group represented by General Formula (II):

$$\text{—}C(=O)\text{—}CH_2\text{—}C(=O)\text{—}Ar\text{—}R \qquad (I).$$

* * * * *